(12) United States Patent
Ahn et al.

(10) Patent No.: US 10,393,672 B2
(45) Date of Patent: Aug. 27, 2019

(54) SYSTEM AND METHOD OF INSPECTING SUBSTRATE AND METHOD OF FABRICATING SEMICONDUCTOR DEVICE USING THE SAME

(71) Applicant: SAMSUNG ELECTRONICS CO., LTD., Suwon-si, Gyeonggi-Do (KR)

(72) Inventors: Jeongho Ahn, Hwaseong-si (KR); Jae-Man Oh, Hwaseong-si (KR); Seongsil Lee, Hwaseong-si (KR); Yusin Yang, Seoul (KR); Dongchul Ihm, Suwon-si (KR); Hyungsuk Cho, Hwaseong-si (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 0 days.

(21) Appl. No.: 15/959,347

(22) Filed: Apr. 23, 2018

(65) Prior Publication Data
US 2019/0033232 A1    Jan. 31, 2019

(30) Foreign Application Priority Data
Jul. 28, 2017  (KR) .................. 10-2017-0096434

(51) Int. Cl.
| G02B 21/00 | (2006.01) |
| G01N 21/95 | (2006.01) |
| G01N 21/88 | (2006.01) |
| G01N 21/956 | (2006.01) |
| G11C 29/02 | (2006.01) |
| H01J 37/28 | (2006.01) |
(Continued)

(52) U.S. Cl.
CPC ..... *G01N 21/9501* (2013.01); *G01N 21/8806* (2013.01); *G01N 21/956* (2013.01); *G02B 21/002* (2013.01); *G11C 29/02* (2013.01); *H01J 37/263* (2013.01); *H01J 37/28* (2013.01); *G11C 2029/0403* (2013.01)

(58) Field of Classification Search
CPC .......... G01N 21/9501; G01N 21/8806; G01N 21/956; G02B 21/002; G11C 29/02; G11C 2029/0403; H01J 37/263; H01J 37/28
USPC .................. 356/609, 614–624, 237.2–237.6
See application file for complete search history.

(56) References Cited

U.S. PATENT DOCUMENTS

| 5,248,876 A | 9/1993 | Kerstens et al. |
| 5,960,107 A * | 9/1999 | Leroux ............... G01B 11/306 |
| | | 356/618 |
(Continued)

*Primary Examiner* — Isiaka O Akanbi
(74) *Attorney, Agent, or Firm* — Volentine, Whitt & Francos, PLLC

(57) ABSTRACT

A substrate inspection system includes a substrate support, optics configured to irradiate a patterned structure on the substrate and capture images of the patterned structure from light reflected from the patterned structure, a focus adjustment operative to adjust a focal position of the incident light on the patterned structure, and an image processor configured to calculate an optimal value of a focus offset used to establish focal points of the light for defect detection in the patterned structure. The patterned structure may include a first pattern having an opening and a second pattern having top surfaces located at different heights relative to the substrate. The value of the focus offset is determined using images of the top surfaces of the second pattern obtained while changing the focal position of the incident light.

20 Claims, 21 Drawing Sheets

(51) Int. Cl.
  *H01J 37/26* (2006.01)
  *G11C 29/04* (2006.01)

(56) References Cited

U.S. PATENT DOCUMENTS

| | | | |
|---|---|---|---|
| 6,154,574 A * | 11/2000 | Paik | G06T 5/003 |
| | | | 250/201.2 |
| 7,449,898 B2 | 11/2008 | Honda et al. | |
| 8,243,273 B2 | 8/2012 | Levinski et al. | |
| 8,605,275 B2 | 12/2013 | Chen et al. | |
| 9,158,613 B2 | 10/2015 | Jeon et al. | |
| 9,606,452 B2 * | 3/2017 | Jung | G03F 7/70625 |
| 9,696,264 B2 | 7/2017 | Lange et al. | |
| 9,726,617 B2 | 8/2017 | Kolchin et al. | |
| 2006/0234136 A1 * | 10/2006 | Kim | G03F 1/44 |
| | | | 430/5 |
| 2010/0188486 A1 | 7/2010 | Amanullah et al. | |
| 2011/0164865 A1 * | 7/2011 | Hamada | G02B 7/365 |
| | | | 396/91 |
| 2012/0164763 A1 * | 6/2012 | Fukazawa | G01N 21/9501 |
| | | | 438/16 |
| 2014/0152796 A1 | 6/2014 | Mitsuhiro et al. | |
| 2015/0332452 A1 | 11/2015 | Tsuchiya et al. | |
| 2016/0305892 A1 | 10/2016 | Tsuchiya | |

* cited by examiner

< Focus Offset Image >

< Focus offset images obtained at focal positions >

SYSTEM AND METHOD OF INSPECTING SUBSTRATE AND METHOD OF FABRICATING SEMICONDUCTOR DEVICE USING THE SAME

PRIORITY STATEMENT

This U.S. non-provisional patent application claims priority under 35 U.S.C. § 119 to Korean Patent Application No. 10-2017-0096434, filed on Jul. 28, 2017, in the Korean Intellectual Property Office, the entire contents of which are hereby incorporated by reference.

BACKGROUND

The inventive concept relates to a substrate inspection system, a substrate inspection method and to a method of fabricating a semiconductor device using the same for quality control purposes. In particular, the inventive concept relates to a system and a method of detecting pattern defects on a substrate and to a method of fabricating a semiconductor device using the same.

It is necessary to detect manufacturing defects in semiconductor devices so that reliability and process yield of the semiconductor device may be improved. To this end, defects are generally detected by an optical method. However, as the complexity of the process of manufacturing semiconductor devices increases, the patterns and features of the devices become finer and the architecture of the devices becomes more complex, it becomes increasingly difficult to properly detect and classify various types of defects that may occur.

SUMMARY

According to the inventive concept, a substrate inspection system may include a supporting structure configured to support and move a substrate, an optical structure configured to provide an incident light to the substrate, to receive a reflection light reflected by the substrate, to obtain images from the reflection light, and to detect a defect of a pattern on the substrate, the pattern including a first pattern having an opening and a second pattern having top surfaces located at different heights, the opening extending in a direction perpendicular to a top surface of the substrate, a focus adjusting structure configured to adjust a focal position of the incident light provided to the substrate, and an image processing structure configured to calculate an optimal value of a focus offset from images of the top surfaces of the second pattern, the images of the top surface of the second pattern being obtained while changing the focal position of the incident light provided to the substrate.

According to the inventive concept, an inspection method for use in quality control of semiconductor devices may include determining an optimal focus offset value, irradiating a layered structure on a substrate with incident light focused based on the optimal focus offset value, capturing an image of the layered structure from light reflected from the layered structure as a result of the irradiating of the layered structure, and detecting for a defect in the layered structure using the captured image of the layered structure, and in which the layered structure comprises a first pattern having a top surface and an opening therein and a second pattern having top surfaces located at different heights relative to a top surface of the substrate, and the opening extends in a direction perpendicular to a top surface of the substrate from the top surface of the first pattern. The optimal focus offset value is determined by a routine that includes capturing focus offset images each of a region of the layered structure including the top surfaces of the second pattern while changing a focal position of the incident light, whereby the focus offset images are captured at different focal positions of the incident light, and calculating the optimal focus offset value using the focus offset images.

According to the inventive concept, a method of fabricating a semiconductor device may include forming a preliminary structure comprising a stack of layers on a substrate, patterning the preliminary structure to form a layered structure having a staircase portion constituted by ends of the layers, and a pattern of vertical holes in the layers to expose the substrate, and performing a substrate inspection process. The substrate inspection process includes determining an optimal focus offset value, irradiating the layered structure with incident light focused based on the optimal focus offset value, capturing an image of the pattern of vertical holes from light reflected from the layered structure as a result of the irradiating of the layered structure, and detecting for a defect in the vertical holes using the captured image of the pattern of vertical holes. The optimal focus offset value is determined by a routine that includes capturing focus offset images each of a region of the layered structure including top surfaces of the ends of the layers while changing the focal position of the incident light, whereby the focus offset images are captured at different focal positions of the incident light, and calculating the optimal focus offset value using the focus offset images.

According to the inventive concept, an inspection method for use in quality control of semiconductor devices may include providing a target for inspection including a substrate and a layered structure on the substrate and having a pattern of openings exposed at a top surface of the layered structure and a stepped portion having exposed top surfaces disposed at different levels relative to the substrate, determining an optimal focus offset value, imaging the layered structure based on the optimal focus offset value to obtain a representation of the pattern of openings, and analyzing the representation of the pattern of holes to determine whether a defect is present in a region of the layered structure including the pattern of holes. The optimal focus offset value is determined by a routine that includes irradiating a region of the layered structure including the top surfaces of the stepped portion with incident light focused at a focal position spaced a distance from a top surface of the substrate, incrementally changing the focal position to vary the distance at which the focal position is spaced from the top surface of the substrate, capturing an image of said region of the layered structure at each time the focal position has been incrementally changed, whereby a plurality of focus offset images are acquired, and calculating the optimal focus offset value using the focus offset images. Each of the focus offset images is an image of the region of the layered structure captured from light reflecting from the layered structure as a result of the layered structure having been irradiated with the incident light focused at a respective focal position.

BRIEF DESCRIPTION OF THE DRAWINGS

The inventive concept will be more clearly understood from the following brief description of examples thereof taken in conjunction with the accompanying drawings. The accompanying drawings represent non-limiting examples as described herein.

It should be noted that these figures are intended to illustrate the general characteristics of methods, structure and/or materials utilized in certain example examples and to supplement the written description provided below. These drawings are not, however, to scale and may not precisely reflect the precise structural or performance characteristics of any given example, and should not be interpreted as defining or limiting the range of values or properties encompassed by the inventive concept. For example, the relative thicknesses and positioning of molecules, layers, regions and/or structural elements may be reduced or exaggerated for clarity. The use of similar or identical reference numbers in the various drawings is intended to indicate the presence of a similar or identical element or feature.

DETAILED DESCRIPTION

Examples of the inventive concept will now be described more fully with reference to the accompanying drawings.

Figure 1:
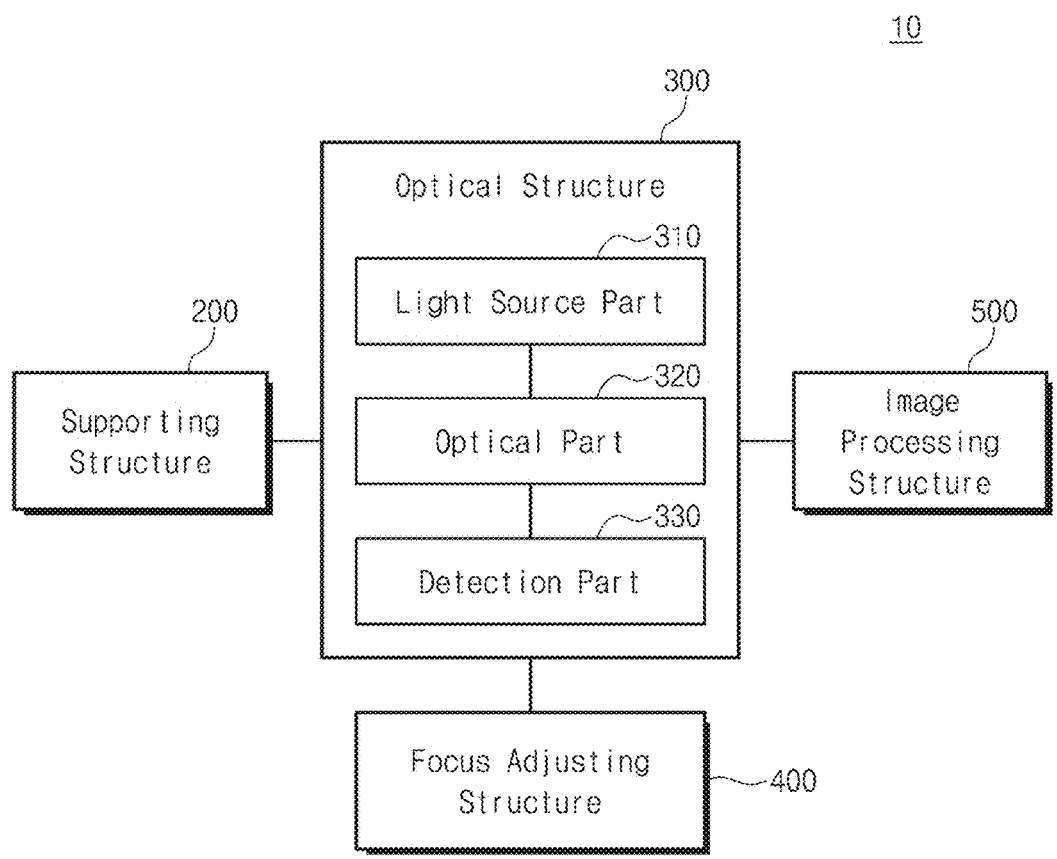
FIG. 1 is a block diagram of examples of a substrate inspection system according to the inventive concept.
Figure 2:
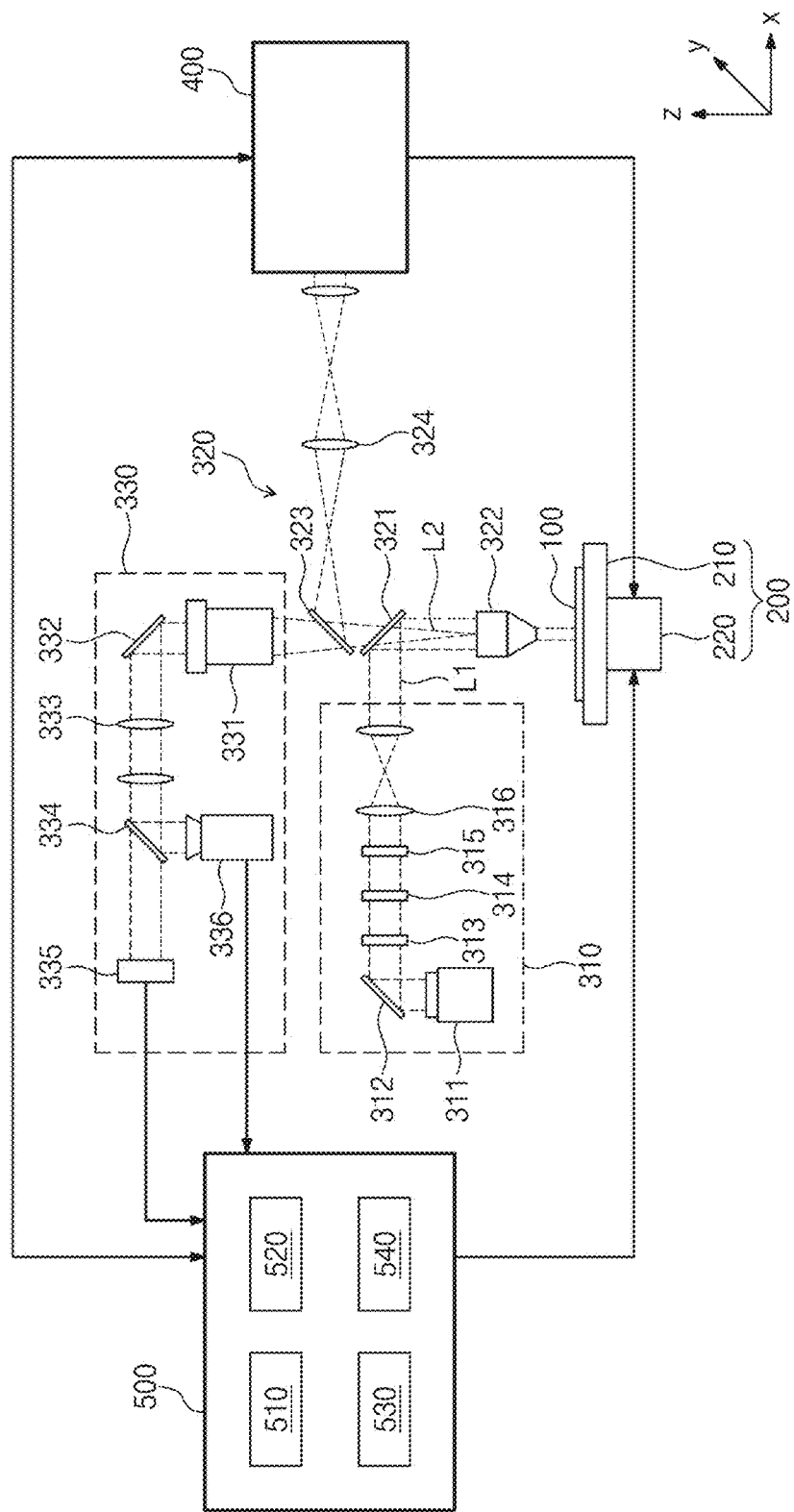
FIG. 2 is a schematic diagram of an example of the substrate inspection system illustrated by FIG. 1.

FIG. 1 is a block diagram of a substrate inspection system according to the inventive concept. FIG. 2 is a diagram schematically illustrating a substrate inspection system depicted by FIG. 1.

Referring to FIGS. 1 and 2, a substrate inspection system 10 may be an optical inspection system that is configured to provide an incident light L1 to a substrate 100, to receive a reflection light L2 reflected from the substrate 100, to obtain an image from the reflection light L2, and to analyze the reflection light L2 to determine whether there are defects on the substrate 100. For example, the substrate inspection system 10 may include a bright-field illumination inspection system, dark-field illumination inspection system, or a laser scanning inspection system. The substrate 100 basically refers in general to a target of or object for inspection by the inspection system and may be or include a semiconductor substrate, such as a wafer, on which various patterns constituting a semiconductor device are formed. The patterns may be three-dimensional structures, such as holes, grooves, trenches, and/or line-and-space patterns. In certain examples, the substrate 100 may be a glass substrate, but the inventive concept is not limited thereto. According to some examples of the inventive concept, the substrate inspection system 10 may be used to detect defects from various semiconductor devices (e.g., semiconductor packages, semiconductor chips, and display panels) requiring a three-dimensional inspection process. For the sake of simplicity, the description that follows will refer to an example in which the substrate 100 (i.e., the inspection target) is a semiconductor substrate provided with patterns constituting a semiconductor device.

In some examples, the substrate inspection system 10 may include a supporting structure 200, an optical structure 300, a focus adjusting structure 400, and an image processing structure 500. The optical structure 300 may include, for example, a light source part 310, an optical part 320, and a detection part 330. These parts may be referred to in the alternative as units.

The supporting structure 200 may be configured to support and move the substrate 100 and hence, may simply be referred to as a substrate support. As an example, the supporting structure 200 may include a stage 210, on which the substrate 100 is disposed, and a stage driving part 220, which is connected to a lower portion of the stage 210 and is used to move the stage 210 in horizontal and vertical directions. For example, the stage driving part 220 may be configured to move the stage 210 in each or all of first, second, and third directions x, y, and z that are orthogonal to each other. The focus adjusting structure 400 and the image processing structure 500 may be configured to control a horizontal motion (i.e., on an x-y plane) or vertical motion (i.e., along a z axis) of the stage driving part 220.

The light source part 310 may be configured to generate the incident light L1. In some examples, the incident light L1 may be directed from the light source part 310 to the substrate 100 through the optical part 320. As an example, the light source part 310 includes a light source 311, a first reflection mirror 312, a plurality of filters 313, 314, and 315, and first illumination lenses 316. The light source 311 may be configured to generate the incident light L1. The light source 311 may be a lamp or a laser device, but the inventive concept is not limited thereto. In some examples, the incident light L1 has a relatively short wavelength (e.g., that of ultraviolet light). For example, the incident light L1 may have a wavelength ranging from about 100 nm to about 300 nm. However, the inventive concept is not limited thereto. In certain other examples, the incident light L1 has a relatively long wavelength from the visible to near infrared range. For example, the incident light L1 may have a wavelength ranging from about 700 nm to 900 nm.

The first reflection mirror 312 may be oriented to reflect the incident light L1, which is emitted from the light source 311, toward the optical part 320. The plurality of filters 313, 314, and 315 and the first illumination lenses 316 may be interposed (along an optical axis of the system extending) between the first reflection mirror 312 and the optical part 320. The plurality of filters 313, 314, and 315 may include, for example, a spectral filter 313, a polarizing filter 314, and a neutral density (ND) filter 315. The spectral filter 313 may be configured to allow the incident light L1 with a specific wavelength to pass therethrough. The polarizing filter 314 may be configured to control a polarization state of, i.e., polarize, the incident light L1. The ND filter 315 may be configured to control brightness or intensity of the incident light L1. Each of the filters 313, 314, and 315 may be configured to establish an illumination condition suitable for a desired process environment. At least one of the filters 313, 314, and 315 may be replaceable or be omitted. The first illumination lenses 316 may be configured to collimate the incident light L1 so that rays of the incident light L1 propagate parallel to one another from the filters toward the optical part 320.

The optical part 320 may be configured to transmit the incident light L1 from the light source part 310 to the substrate 100 and to transmit the reflection light L2, which is reflected from the substrate 100, toward the detection part 330 or the focus adjusting structure 400. As an example, the optical part 320 includes a first beam splitter 321, an object lens 322, a second beam splitter 323, and second illumination lenses 324. The first beam splitter 321 may be located on an optical path between the light source part 310 and the supporting structure 200. The first beam splitter 321 may be configured to reflect a part of light incident thereon and to transmit the other part of the light. In other words, the first beam splitter 321 may be configured to reflect the incident light L1, which is transmitted from the light source part 310, to the object lens 322, and to transmit the reflection light L2, which is reflected from the substrate 100 and is transmitted through the object lens 322. For example, the first beam splitter 321 may be or include a half mirror.

The object lens 322 may be configured to focus the incident light L1 on a top surface of the substrate 100 (for example, on a top surface of a pattern formed on the substrate 100 or in the pattern). The location of the focal point of the incident light L1 may be referred to as the focal position. The focal position of the incident light L1 may be changed under the control of the focus adjusting structure 400. The object lens 322 may be configured to receive the reflection light L2 reflected from the substrate 100 and transmit a magnified image of the top surface of the substrate 100. The magnification of the image of the substrate 100 may be determined by a numerical aperture (NA) of the object lens 322 and/or the wavelength of the incident light L1. The object lens 322 may be configured to convert the reflection light L2 to parallel rays of light. Although not shown, an aperture (not shown) may be provided between the first beam splitter 321 and the object lens 322 to adjust an amount of the incident light L1 directed into the object lens 322.

The second beam splitter 323 may be disposed (optically) in front of the first beam splitter 321. The second beam splitter 323 may be configured to reflect a part of the reflection light L2, which is reflected by the first beam splitter 321, toward the focus adjusting structure 400 and to transmit the other part of the reflection light L2 toward the detection part 330. For example, the second beam splitter 323 may be or include a half mirror. The second illumination lenses 324 may be optically interposed between the second beam splitter 323 and the focus adjusting structure 400. The second illumination lenses 324 may be configured to cause the rays of the reflection light L2, which is reflected by the second beam splitter 323, to propagate parallel to one another toward the focus adjusting structure 400.

The detection part 330 may be configured to obtain an image of the substrate 100 (i.e., an image of the pattern formed on the substrate 100) from the light reflected from the substrate 100. In some examples, the detection part 330 may include a magnifying-power adjusting device 331, a second reflection mirror 332, relay lenses 333, a third beam splitter 334, a first detector 335, and a second detector 336.

The magnifying-power adjusting device 331 may be configured to allow the reflection light L2 passing through the second beam splitter 323 to form an image on the second reflection mirror 332. The magnifying-power adjusting device 331 may include a single zoom lens or a plurality of tube lenses having different magnifications. In the case in which the magnifying-power adjusting device 331 is a single zoom lens, a focal point of the zoom lens may be adjusted to allow the detection part 330 to obtain an optimized image of the substrate 100. In the case in which the magnifying-power adjusting device 331 includes a plurality of tube lenses, one of the tube lenses may be selected to allow the detection part 330 to obtain an optimized image of the substrate 100.

The second reflection mirror 332 may be disposed (optically) in front of the magnifying-power adjusting device 331. The second reflection mirror 332 may be configured to reflect the reflection light L2 from the magnifying-power adjusting device 331 toward the third beam splitter 334. The relay lenses 333 may be interposed (optically) between the second reflection mirror 332 and the third beam splitter 334. The relay lenses 333 may allow for a certain spacing to be established between the second reflection mirror 332 and the third beam splitter 334. Between the relay lenses 333, the reflection light L2 may propagate without a change in beam size. In certain examples, the relay lenses 333 may be configured to invert an image of the reflection light L2. The third beam splitter 334 may be configured to split the reflection light L2 into two light beams propagating toward the first and second detectors 335 and 336, respectively. For example, the third beam splitter 334 may be configured to transmit a part of the reflection light L2, which is reflected by the second reflection mirror 332, toward the first detector 335 and to reflect the other part of the reflection light L2 toward the second detector 336. For example, the third beam splitter 334 may be or include a half mirror.

The first detector 335 may be configured to produce an image of the substrate 100, which will be used for a defect inspection process. In some examples, the first detector 335 includes a TDI camera or a charge coupled device (CCD) camera. The image of the defect inspection process may be a digital image having a relatively high signal-to-noise ratio (SNR), and the presence or absence of defect may be determined by analyzing such an image using an inspection algorithm. The second detector 336 may be used to observe or review the substrate 100. Also, the second detector 336 may be used for a small pattern and/or precise alignment. In certain examples, when the process of detecting for defects is finished, the second detector 336 may be used to review a detected defect.

The focus adjusting structure 400 may be disposed at a side of the supporting structure 200. For example, the focus adjusting structure 400 may be arranged at a position facing the light source part 310. The focus adjusting structure 400 may be configured to receive a part of the reflection light L2, which is reflected from the substrate 100, and thereby to collect information on a focal position of the incident light L1. The focus adjusting structure 400 may control the focal position of the incident light L1 directed toward the substrate 100, based on the collected information regarding the focal position. In some examples, the focus adjusting structure 400 may change the focal position of the incident light L1 by changing a position of the substrate 100 in the third direction z (i.e., changing the distance between the object lens 322 and the substrate 100) using the stage driving part 220. However, the inventive concept is not limited thereto. The focus adjusting structure 400 may change the focal position using various methods. As an example, to change the focal position of the incident light L1, a position of the object lens 322 in the third direction z may be changed by the focus adjusting structure 400. In certain examples, to change the focal positions of the incident light L1, the wavelength or propagation path of light emitted from of the light source 311 may be adjusted by the focus adjusting structure 400. The focus adjusting structure 400 may be configured to feed back the collected information regarding the focal position to the image processing structure 500 in real time.

The image processing structure 500 may be configured to calculate an optimal value of the focus offset according to a vertical position of a defect desired to be detected and to determine a focal position optimized for a defect detection process. For example, in the case in which the patterns formed on the substrate 100 have top surfaces located at different heights (i.e., in the case in which the patterns form a stepped or staircase structure), the optimal value of the focus offset may be calculated from images of the top surfaces of the steps of the stepped or staircase structure. This will be described in more detail with reference to a substrate inspection method.

According to some examples of the inventive concept, the image processing structure 500 includes a controller 510, a memory device 520, an input/output unit 530, and an interface unit 540. The controller 510 may execute various operations (e.g., selecting a comparison region in each of focus offset images, conduct image analysis of the comparison regions, and so forth) for calculating the optimal value of the focus offset. In other words, the calculation of the optimal value of the focus offset may be performed using specific algorithms executed by the controller 510. For example, the image processing structure 500 may be configured to include a computer system, in which a program containing an algorithm for calculating an optimized focus offset is installed.

The memory device 520 may be configured to store various data (e.g., information regarding a layout of patterns on the substrate 100, information regarding a vertical position of a defect desired to be detected, focus offset images, images of the comparison region, and so forth), which may be used to calculate the optimal value of the focus offset. In addition, the memory device 520 may be used to store additional data (e.g., an optimized focus offset value, information on focal points of the incident light L1, and so forth), which are processed by the controller 510 or the focus adjusting structure 400. The memory device 520 may include a nonvolatile storage device. As examples, the memory device 520 includes at least one of a hard disk drive and/or a nonvolatile semiconductor memory device (e.g., a FLASH memory device, a phase-change memory device, a magnetic memory device, and so forth).

The input/output unit 530 may include a keyboard, keypad, and/or display device. Image data obtained by the optical structure 300 may be transmitted to the image processing structure 500 through the interface unit 540. In addition, data processed by the image processing structure 500 may be transmitted to the focus adjusting structure 400 or to other external device through the interface unit 540. The interface unit 540 may include a wired element, a wireless element, a universal serial bus (USB) port, and so forth. The controller 510, the memory device 520, the input/output unit 530, and the interface unit 540 may be coupled to each other via at least one data bus. Hereinafter, a substrate inspection method using the substrate inspection system 10 will be described in more detail.

Figure 3:
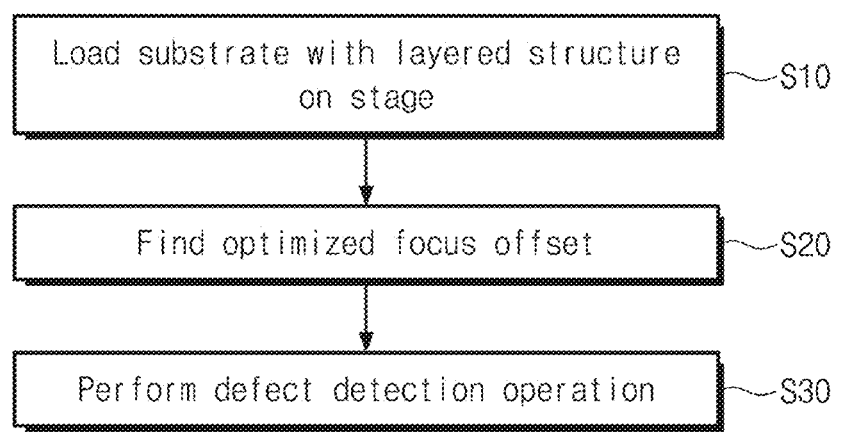
FIG. 3 is a flow chart illustrating an example of a substrate inspection method according to the inventive concept.
Figure 4A:
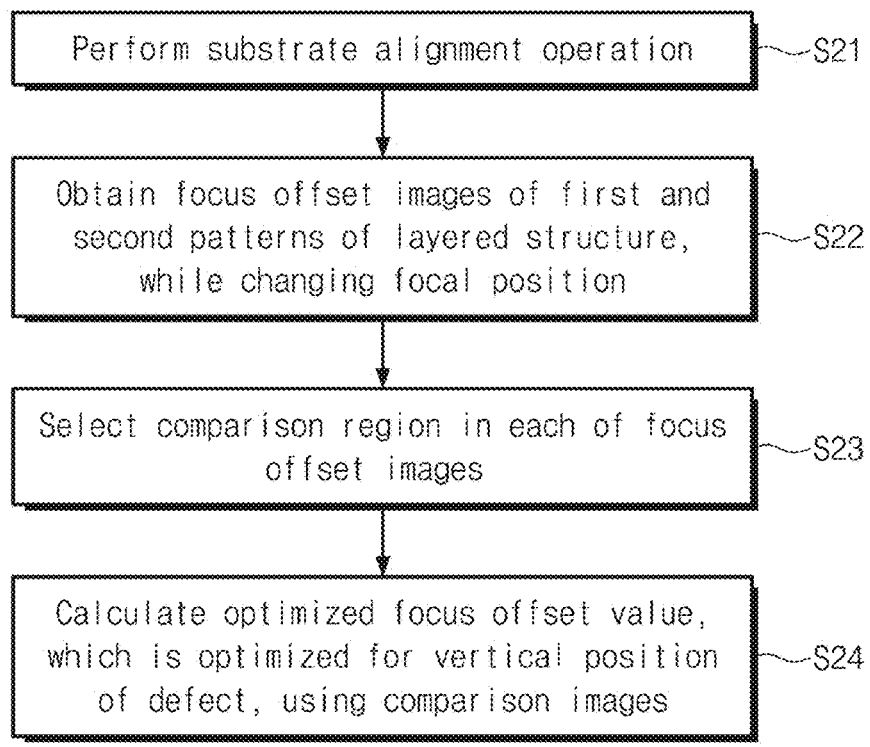
FIG. 4A is a flow chart illustrating in detail a routine of step S20 of the method illustrated in FIG. 3.
Figure 4B:
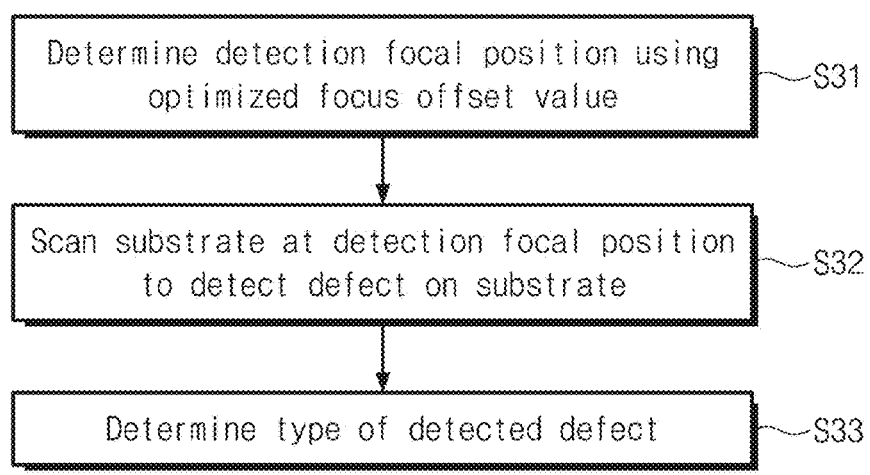
FIG. 4B is a flow chart illustrating in detail a routine of step S30 of FIG. 3.
Figure 5:
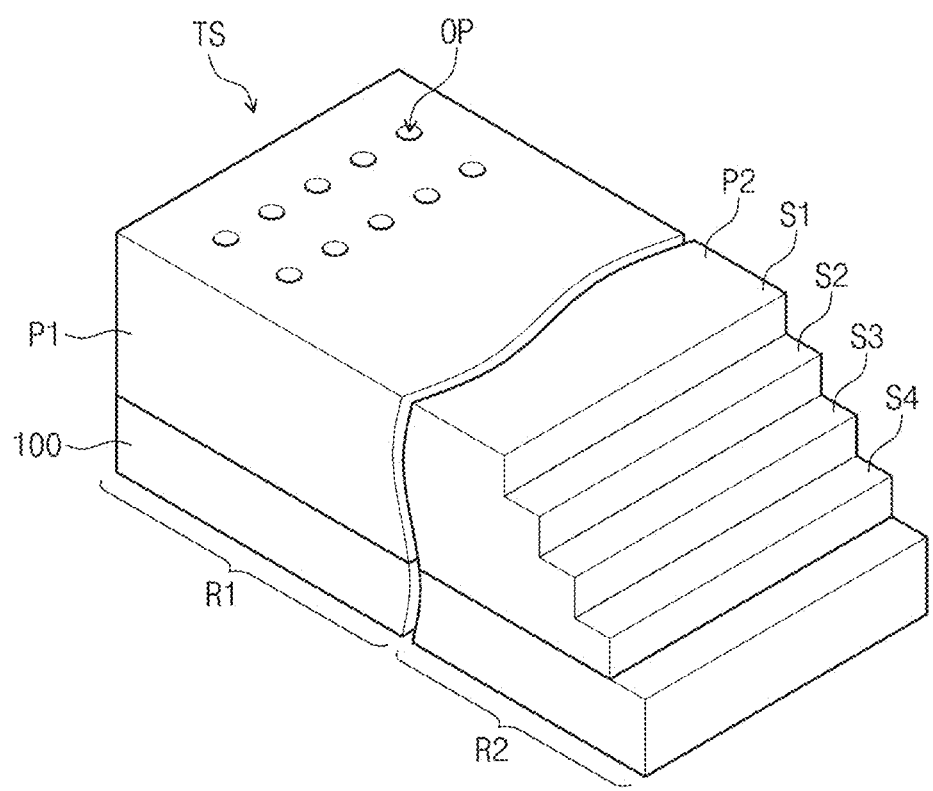
FIG. 5 is a perspective view of an inspection target (e.g., a substrate).
Figure 6:
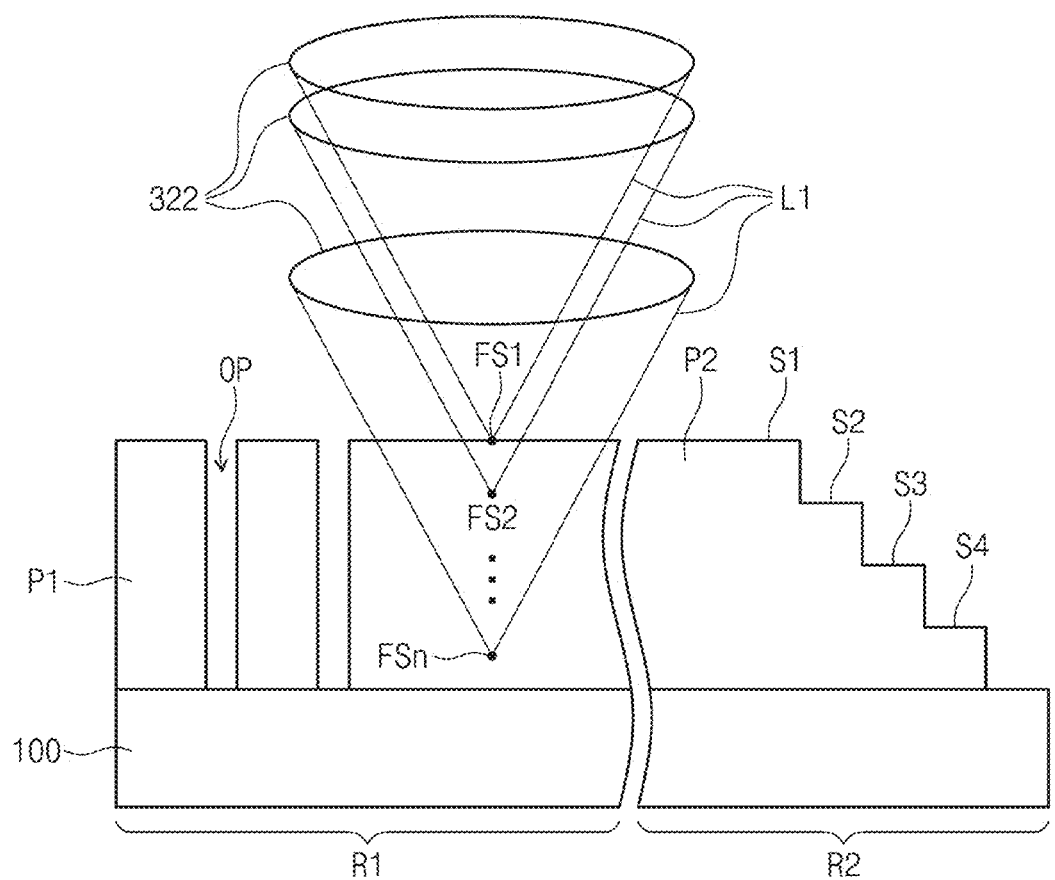
FIG. 6 is a conceptual diagram illustrating a process for determining an optimized focus offset value.
Figure 7:
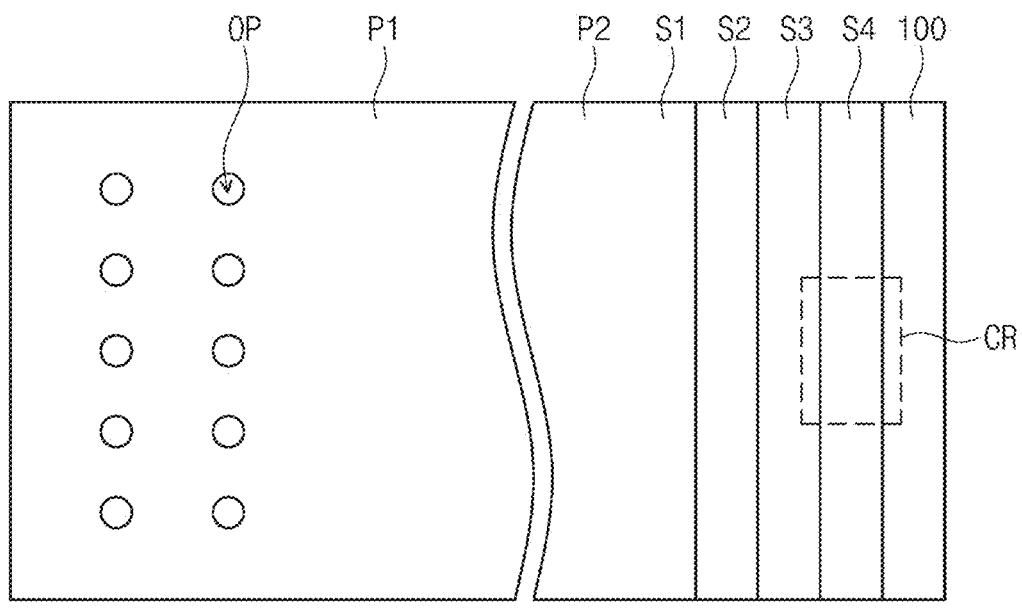
FIG. 7 is a diagram of a focus offset image obtained from the substrate of FIG. 5.
Figure 8:
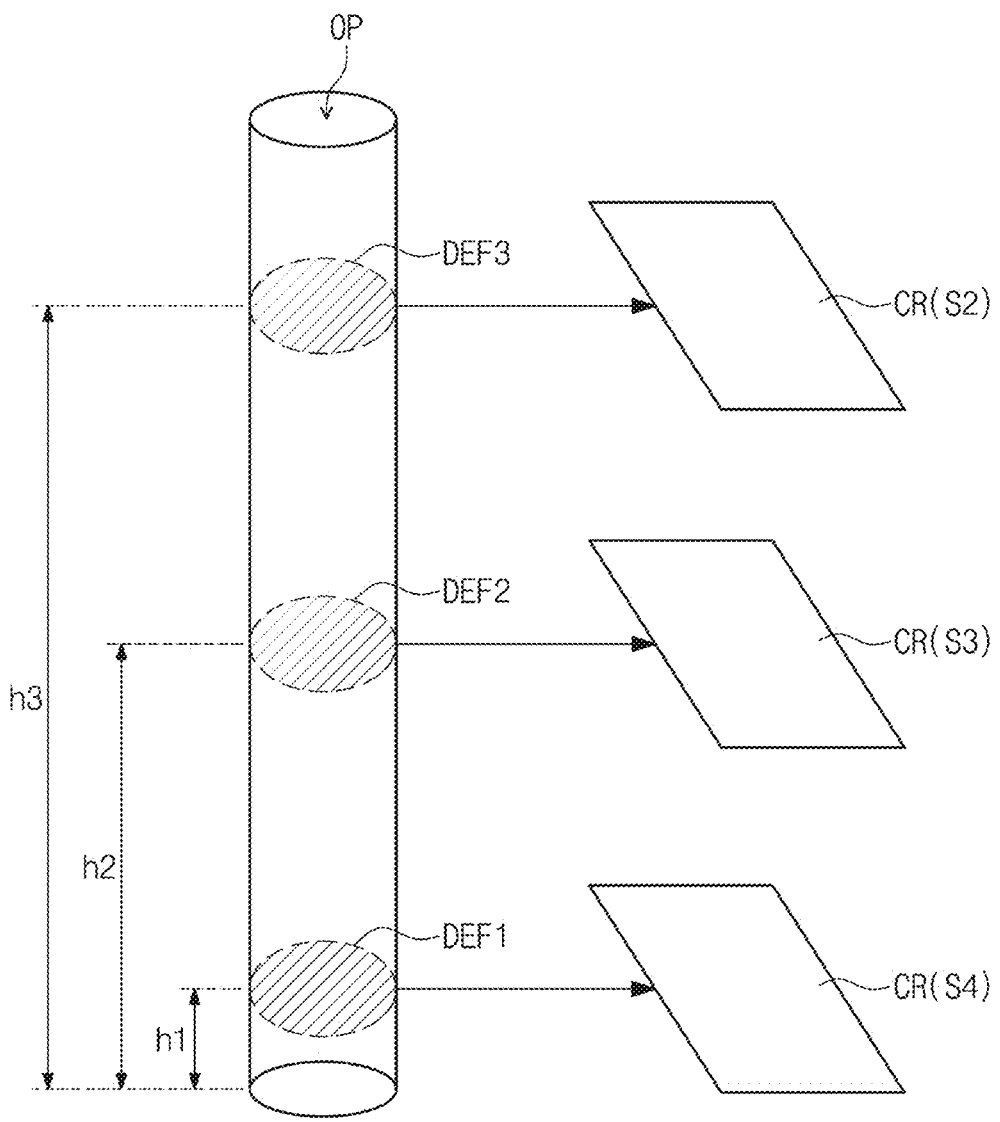
FIG. 8 is a conceptual diagram illustrating a method of selecting a comparison region from a focus offset image.
Figure 9:
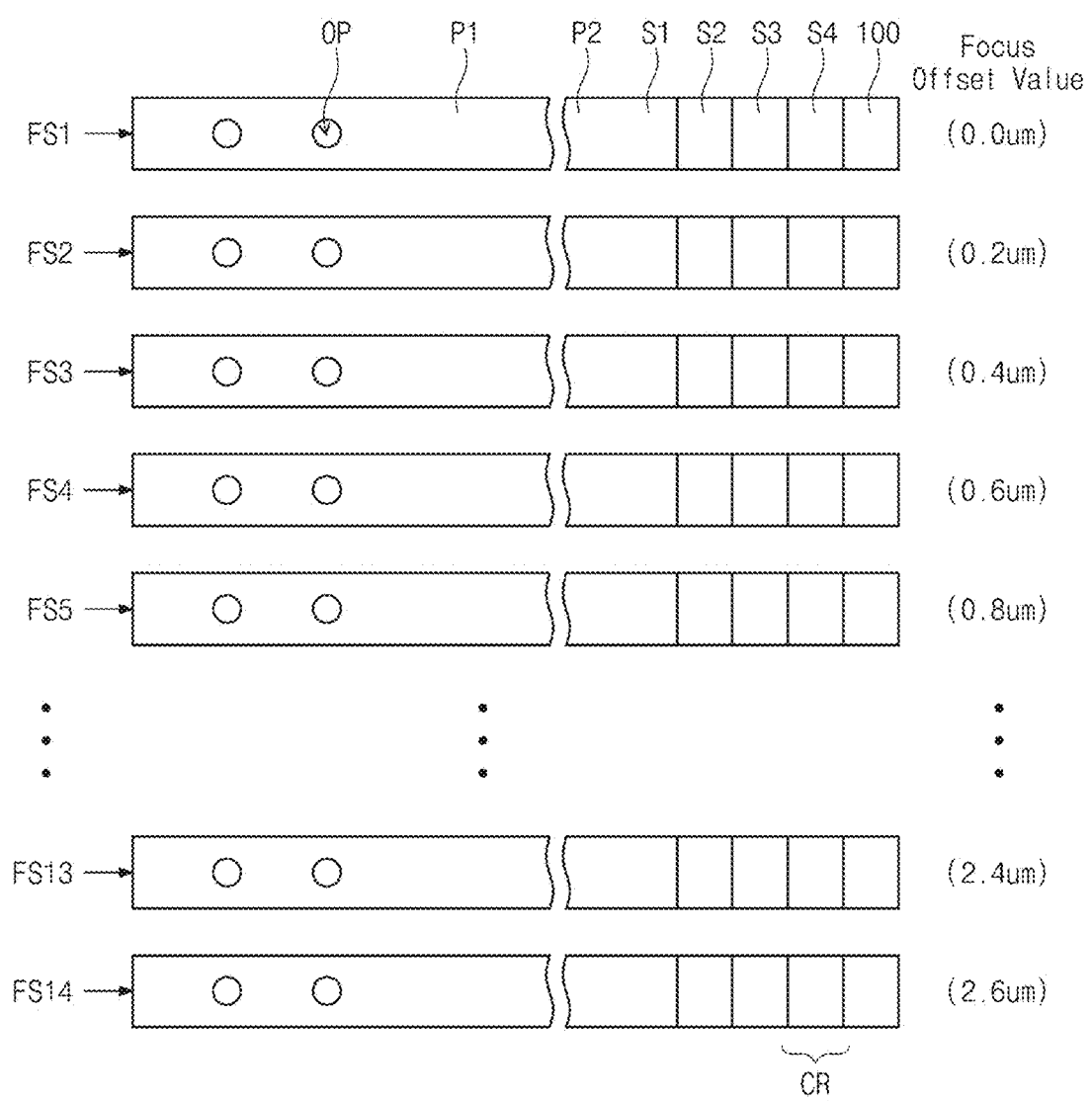
FIG. 9 is a diagram illustrating focus offset images according to focal positions.
Figure 10:
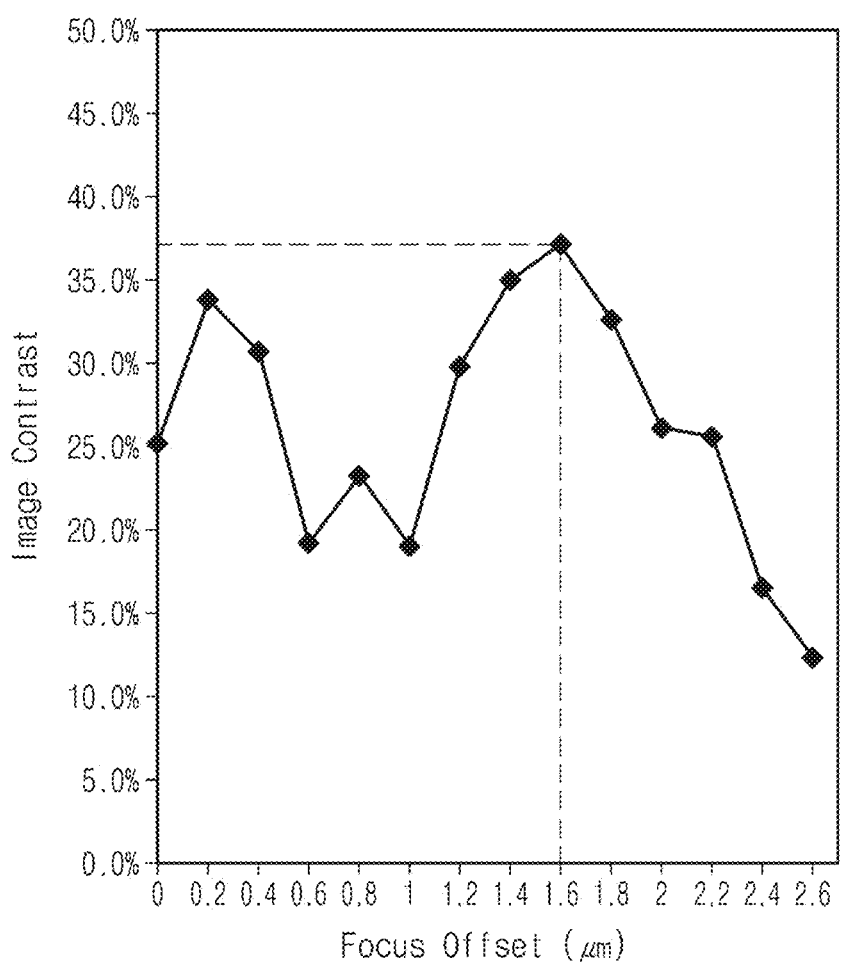
FIG. 10 is a graph of image contrast values at focus offset values corresponding to the comparison images of FIG. 9.
Figure 11:
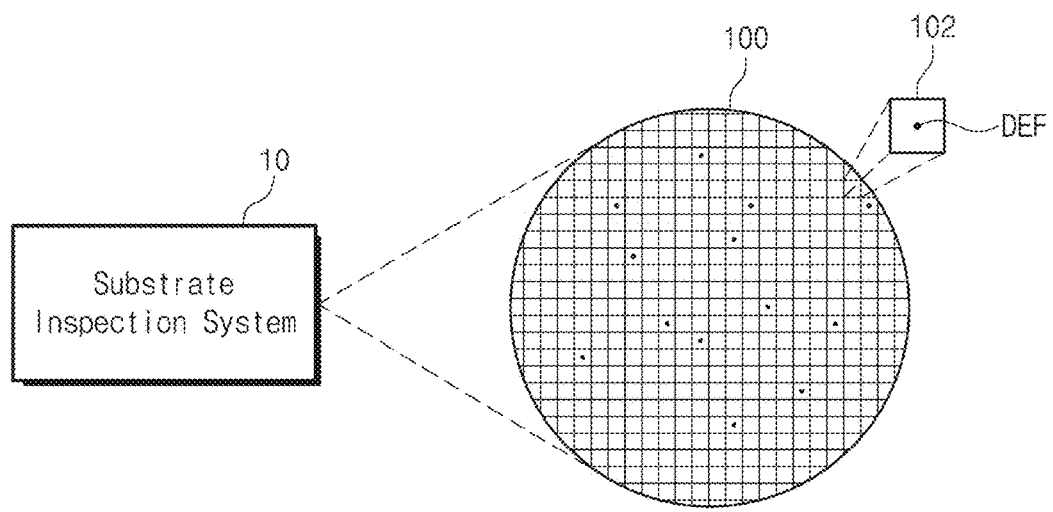
FIG. 11 is a conceptual diagram illustrating a process for detecting defects.

FIG. 3 is a flow chart illustrating in general a substrate inspection method according to the inventive concept. FIG. 4A is a flow chart illustrating in detail a step S20 of FIG. 3. FIG. 4B is a flow chart illustrating in detail a step S30 of FIG. 3. FIG. 5 is a perspective view of an inspection target (e.g., a substrate). FIG. 6 is a diagram schematically illustrating a process for determining an optimized focus offset value. FIG. 7 is a diagram illustrating a focus offset image obtained from the substrate of FIG. 5. FIG. 8 is a diagram illustrating a method of selecting a comparison region from a focus offset image. FIG. 9 is a diagram illustrating focus offset images according to focal positions. FIG. 10 is a graph showing image contrast values at focus offset values corresponding to the comparison images of FIG. 9. FIG. 11 is a diagram illustrating a process for detecting defects.

Referring to FIGS. 1, 2, 3, and 5, the substrate inspection method may include loading the substrate 100, on which a layered structure TS is formed, on the stage 210 (in S10), finding an optimal value of a focus offset (in S20), and performing a defect detection operation (in S30).

The layered structure TS may include a plurality of insulating and/or conductive layers stacked on the substrate 100. In some examples, the layered structure TS includes a first pattern P1 formed on a first region R1 of the substrate 100 and a second pattern P2 formed on a second region R2 of the substrate 100. The first pattern P1 may include openings OP which extend in a direction perpendicular to the top surface of the substrate 100, and the second pattern P2 may include first to fourth top surfaces S1, S2, S3, and S4 disposed at different heights or levels in the layered structure TS. For example, the openings OP may be open holes which extend through the layered structure TS and expose the substrate 100, but the inventive concept is not limited to inspecting such a structure. In certain examples, the openings OP may be trenches or grooves (recesses). Leading edges of the first to fourth top surfaces S1, S2, S3, and S4 in a given direction from the first pattern P1 may be offset horizontally from one another, thereby forming a staircase portion of the second pattern P2 of the layered structure TS. A top surface of the first pattern P1 may be disposed at the same height as a first top surface S1 of the second pattern P2. In other words, the top surface of the first pattern P1 may be coplanar with the first top surface S1 of the second pattern P2. FIG. 5 illustrates an example in which the staircase portion of the second pattern has four steps, but the inventive concept is not limited thereto. The number of steps of the staircase portion of the second pattern P2 may be four or more.

As a semiconductor device is scaled down, the openings OP may be formed to have a high aspect ratio (i.e., a high ratio of height to width or diameter). For example, the openings OP may be formed to have a high aspect ratio ranging from 1:5 to 1:100. In this case, it may not be easy to realize high process uniformity in an etching process for forming the openings OP. This may lead to a pattern failure (abnormal formation) of the openings OP during the etching process. Pattern failure of the openings OP may refer to non-uniformity in the shapes of the openings OP. As examples of pattern failure, the openings OP may have non-uniform heights or depths, non-uniform aspect ratios such as non-uniform ratios of height to diameter in the case in which the openings OP are circular, variations in the diameters of the openings OP at different vertical positions, a bridging between the openings OP, or one or more of the openings OP not exposing the substrate as desired ("not-open" failure). A substrate inspection method, according to some examples of the inventive concept, may be used to effectively detect the above-described pattern failures of the openings OP.

As a semiconductor device is scaled down, the size of a region evincing a defect desired to be detected (e.g., a pattern failure of the openings OP) may be on the order of several tens of nm. When an inspection system can vary the focal point of detection light within a range of several tens to several hundreds of nm, a wide array of defect signals have the potential to be produced during the defect detection process. Thus, to improve defect detection ability, a focal point of an optical part of the inspection system should reside on a focus plane or a focal position that is optimized for the defect desired to be detected. The focal point may be considered as a point that is offset from a reference position along an optical axis between the optical part and the substrate and so, the distance between the focal point and the reference position may be defined as the focus offset value or focus offset for short. According to an aspect of the inventive concept there is provided a process of finding a focus offset optimal for detecting a defect, such as a pattern failure, on the substrate.

According to some examples of the inventive concept, the process of finding the optimized focus offset may be performed using an image of the second pattern P2, whose top surface is positioned at a height corresponding to a vertical position of a defect desired to be detected. The process of finding the optimized focus offset will be described in more detail with reference to FIG. 4A and FIGS. 5 to 8.

Referring to FIGS. 1, 2, and 4A and FIGS. 5 to 8, a substrate alignment operation may be performed on the substrate 100 loaded on the stage 210 (in S21). The substrate alignment operation may include adjusting a horizontal position (i.e., position on the x-y plane) of the object lens 322 or the stage 210 to allow the incident light L1 to irradiate the first and second patterns P1 and P2. For example, based on previously-provided information on a layout of the first and second patterns P1 and P2 formed on the substrate 100, the focus adjusting structure 400 or the image processing structure 500 may be configured to change a position of the stage driving part 220 in the first direction x and/or the second direction y, during the substrate alignment operation.

Subsequently, images of the first and second patterns P1 and P2 of the layered structure TS may be obtained while changing focal positions incrementally, for example, (in S22) and these images will be referred to hereinafter as focus offset images. For example, in this imaging of the layered structure TS the incident light L1 may be focused on a plurality of focal positions that are different from a reference focal position and the focus offset image of the first and second patterns P1 and P2 may be obtained at each of the focal positions. The reference focal position may be predetermined, and the focus adjusting structure 400 may adjust a position of the stage 210 in the third direction z to focus the incident light L1 on the reference focal position and changed focal positions. The imaging of the layered structure TS to obtain the focus offset images may be performed using the optical structure 300.

In general, the reference focal position may coincide with a topmost portion of the patterns formed on the substrate 100, but the inventive concept is not limited thereto. In the case in which a vertical position of a defect desired to be detected is known, a position of the defect may be set as the reference focal position. For example, the reference focal position may be one of focal positions FS1, FS2 . . . FSn, shown in FIG. 6. The greater the number of focal positions FS1, FS2 . . . FSn and the smaller the intervals between the focal positions FS1, FS2 . . . FSn, the more exact and reliable the process of finding the optimized focus offset becomes. In the case in which the reference focal position is selected as a point of z=0, the changed focal positions (sum of the increments by which the focal position is changed) may be within a range of ±several μm (in particular, ±3 μm) in the z-axis direction (i.e., the third direction z). Here, a focus offset value may be defined as a vertical (in FIG. 6) distance between the reference focal position and the changed focal position. If the changed focal position becomes closer to the substrate 100 than the reference focal position (i.e., a distance between the object lens 322 and the substrate 100 is decreased), the focus offset value may be defined to have a positive value, and otherwise, the focus offset value may be defined to have a negative value. Each of the focus offset images may be representative of a two-dimensional image of top surfaces S1-S4 of the first and second patterns P1 and P2, as shown in FIG. 7.

A comparison region CR may be selected from each of the focus offset images obtained by step S22 (in S23). The comparison region CR may be a region of the focus offset image of the second pattern P2. More specifically, the comparison region CR may be a region of a focus offset image showing a target surface, which is one of the top surfaces of the second patterns P2 and is positioned at a level most adjacent to a vertical position of a defect desired to be detected. For example, as shown in FIGS. 7 and 8, if it is desired to detect a first defect for a DEF1 located at the first height h1, a region of a focus offset image showing the fourth top surface S4, which is the top surface located at or closest to the first height h1 among the top surfaces S1-S4, may be selected as the comparison region CR. Similarly, if it is desired to detect for a second defect DEF2 located at the second height h2, another region of the focus offset image showing the third top surface S3, which is the top surface located at or closest to the second height h2 among the top surfaces S1-S4, may be selected as the comparison region CR. If it is desired to detect for a third defect DEF3 located at the third height h3, a region of the focus offset image showing the second top surface S2 located at or closest to the third height h3 among the top surfaces S1-S4, may be selected as the comparison region CR. For the substrate 100 loaded on the stage 210, information on a vertical position of a defect desired to be detected may be previously provided to the image processing structure 500. The image processing structure 500 may select a region of the focus offset image as the comparison region CR, based on the previously-provided information. Images of the comparison regions CR may be referred to as comparison images and may be stored in the memory device 520 of the image processing structure 500.

The value of the focus offset, which is optimized for detection of a defect at a desired vertical position within the target of inspection, e.g., the layered structure TS, may be calculated using the images (i.e., comparison images) of the selected comparison region CR (in S24). For example, the calculation of the optimal value of the focus offset may include obtaining a value of the contrast of each of the comparison images obtained at the focal positions and selecting a focus offset value corresponding to a comparison image having the largest contrast value as the optimal value of the focus offset.

For example, if it is desired to detect whether a "not-open" pattern failure has occurred in the forming of the openings OP of the first pattern P1 shown in FIG. 5, focus offset images may be obtained at focal positions FS1, FS2, . . . , and FS14, as shown in FIG. 9, and then, in each of the focus offset images, a region corresponding to the fourth top surface S4 may be selected as the comparison region CR. In this example, the fourth top surface S4 is the lowermost one of the top surfaces S1, S2, S3, and S4 of the second pattern P2. Image contrast values may be calculated from comparison images of the comparison region CR, and the graph of FIG. 10 shows the results obtained by this process. Referring to FIG. 10, when the focus offset value is 1.6 µm, the comparison image has the largest contrast value, and thus, the value of 1.6 µm can be selected as the optimal value of the focus offset. Here, the reference focal position may be a position (e.g., see FS1 of FIG. 6) of the topmost surface of the first and second patterns P1 and P2. The selection of the comparison region CR and the calculation of the optimal value of the focus offset may be executed based on algorithms stored in the image processing structure 500 (i.e., the controller 510). For example, the controller 510 may select a comparison region CR for each of the images of the top surfaces S1, S2, S3, and S4 of the second pattern P2 and calculate the optimal value of the focus offset through an image analysis process, known per se, which quantifies the contrast of an image, in this case, images of the comparison regions CR.

A defect detection process may be performed using the optimal value of the focus offset calculated in the above-described manner (in S30). More specifically, referring to FIG. 4B, the defect detection process may include determining detection focal positions using the optimal value of the focus offset (in S31), scanning the substrate 100 at the determined detection focal positions to detect a defect on a substrate (in S32), and determining a type of the detected defect (in S33).

The detection focal positions may be determined by adding or subtracting the optimal value of the focus offset, which is obtained by steps S21 to S24, to or from the reference focal position. The determined detection focal positions may be set as a focus offset recipe for a defect detection process and may be used as focal positions of the incident light L1 during the scanning of the substrate 100. In other words, during the defect detection process, the incident light L1 may be controlled to be focused on the detection focal positions and this may make it possible to increase the defect detection ability.

The entire top surface of the substrate 100 of the substrate 100 may be scanned, as shown in FIG. 11. The substrate 100 may include a plurality of chip regions 102, and as a result of the scanning of the substrate 100, at least one defect DEF may be detected on the plurality of chip regions 102. The scanning of the substrate 100 may be effected by moving the stage 210, and various scanning methods, such as leap and scan, on-time scan, TDI scan, spot scan, multi-spot scan, and line scan methods, may be used to scan the substrate 100.

In the case in which a defect is detected by the scanning of the substrate 100, images of the region containing the defect may be analyzed to determine the type of defect. The analysis of the defective region may be performed using the second detector 336 or an additional reviewing device (e.g., a scanning electron microscope (SEM)) of the substrate inspection system 10).

Figure 12:
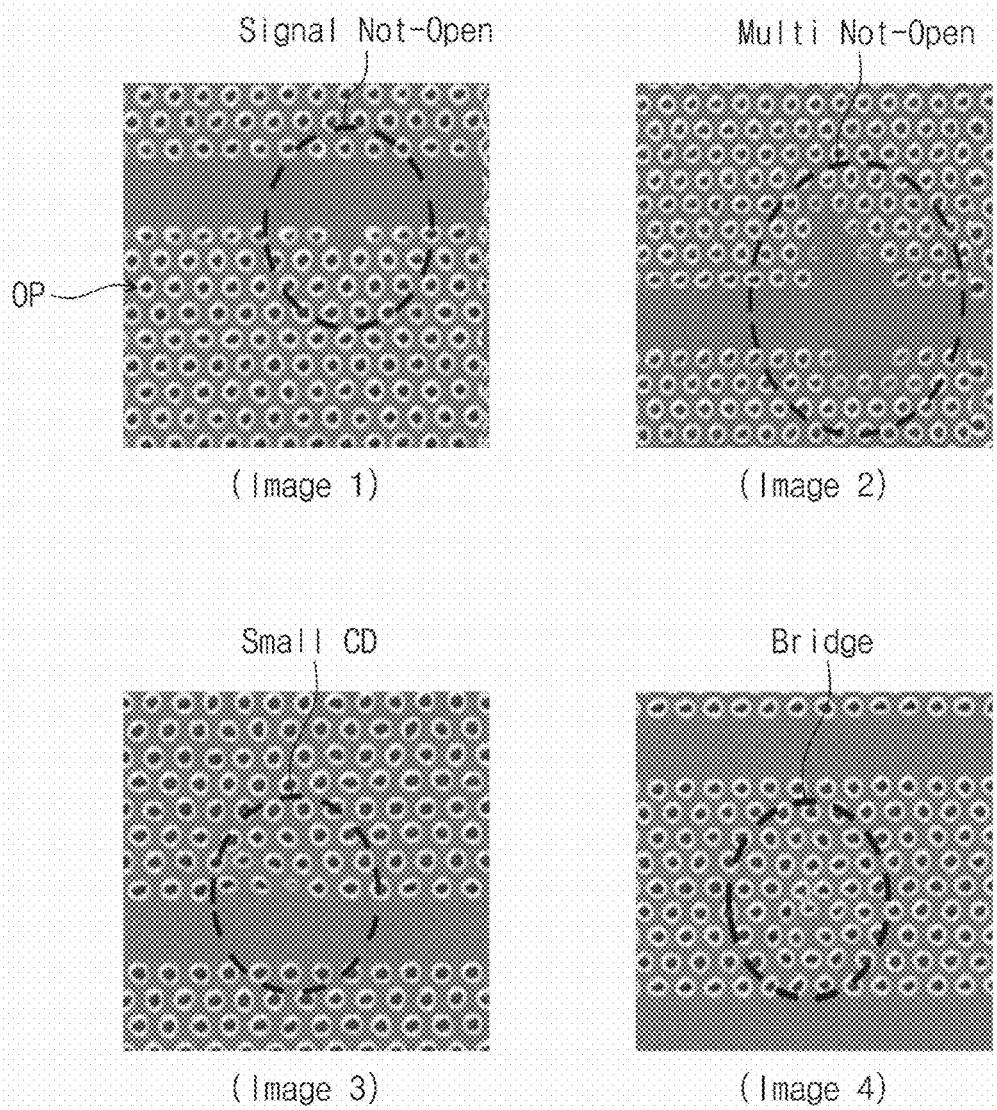
FIG. 12 is a series SEM images showing pattern failures of openings obtained by an example of a substrate inspection method according to the inventive concept.

FIG. 12 includes some examples of SEM images showing pattern failures of openings obtained by a substrate inspection method according to the inventive concept. The substrate inspection method was used to detect pattern failures of the openings OP, and as shown in FIG. 12, there were various pattern failures, such as single not-open (in Image 1), multi not-open (in Image 2), small CD (in Image 3), and bridge (in Image 4). This shows that consistent results can be obtained by the substrate inspection method, according to the inventive concept.

According to one aspect of the inventive concept, when a three-dimensional structure (e.g., a stepwise or staircase structure) is formed on a substrate, the substrate inspection system may easily calculate a focus offset value, which is optimized for a vertical height of a defect desired to be detected, from images of top surfaces of the staircase structure. This can minimize the time it takes to inspect the substrate and to effectively determine whether there has been a failure in the process of producing high-aspect-ratio patterns. Thus, the inventive concept can provide an improved defect detection ability of a substrate inspection system and substrate inspection method.

Figure 13:
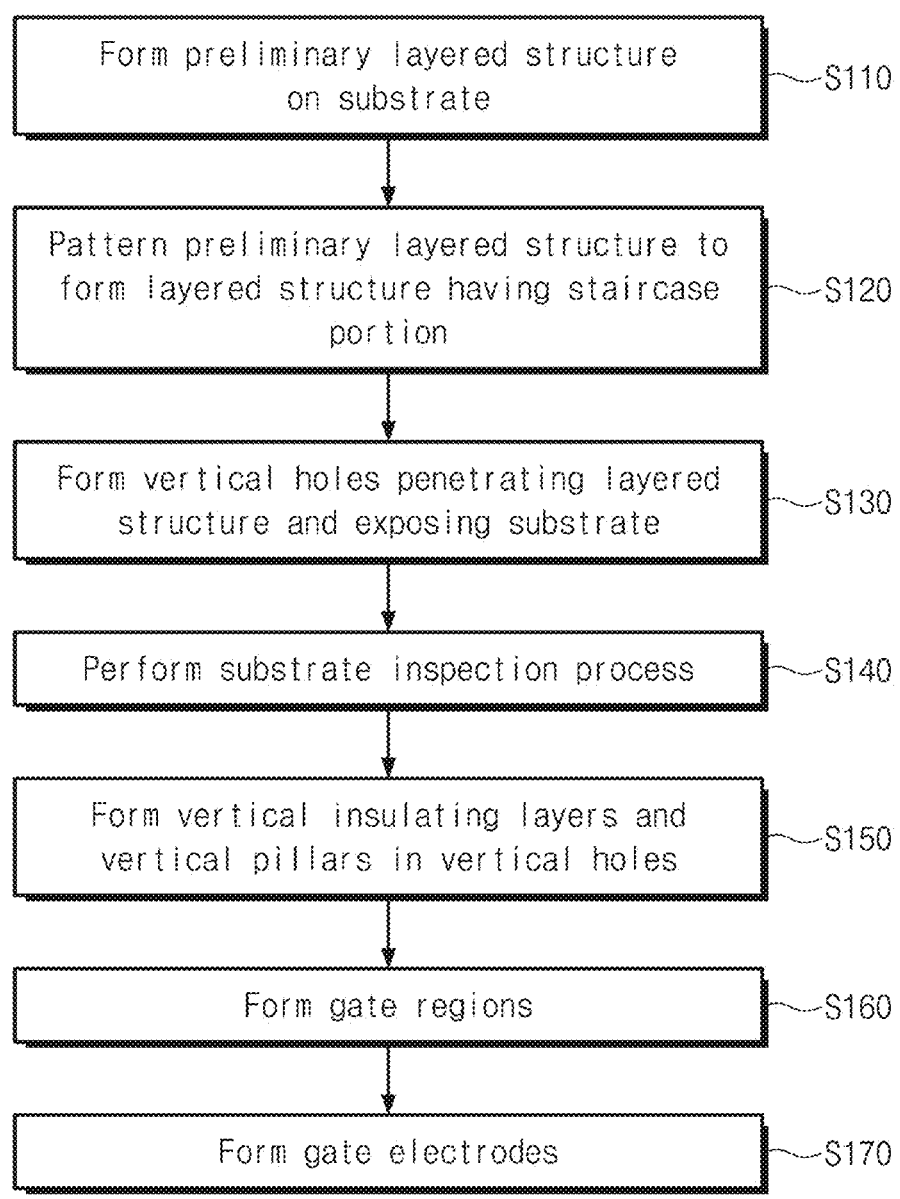
FIG. 13 is a flow chart of a method of fabricating a semiconductor device, according to the inventive concept.
Figure 14:
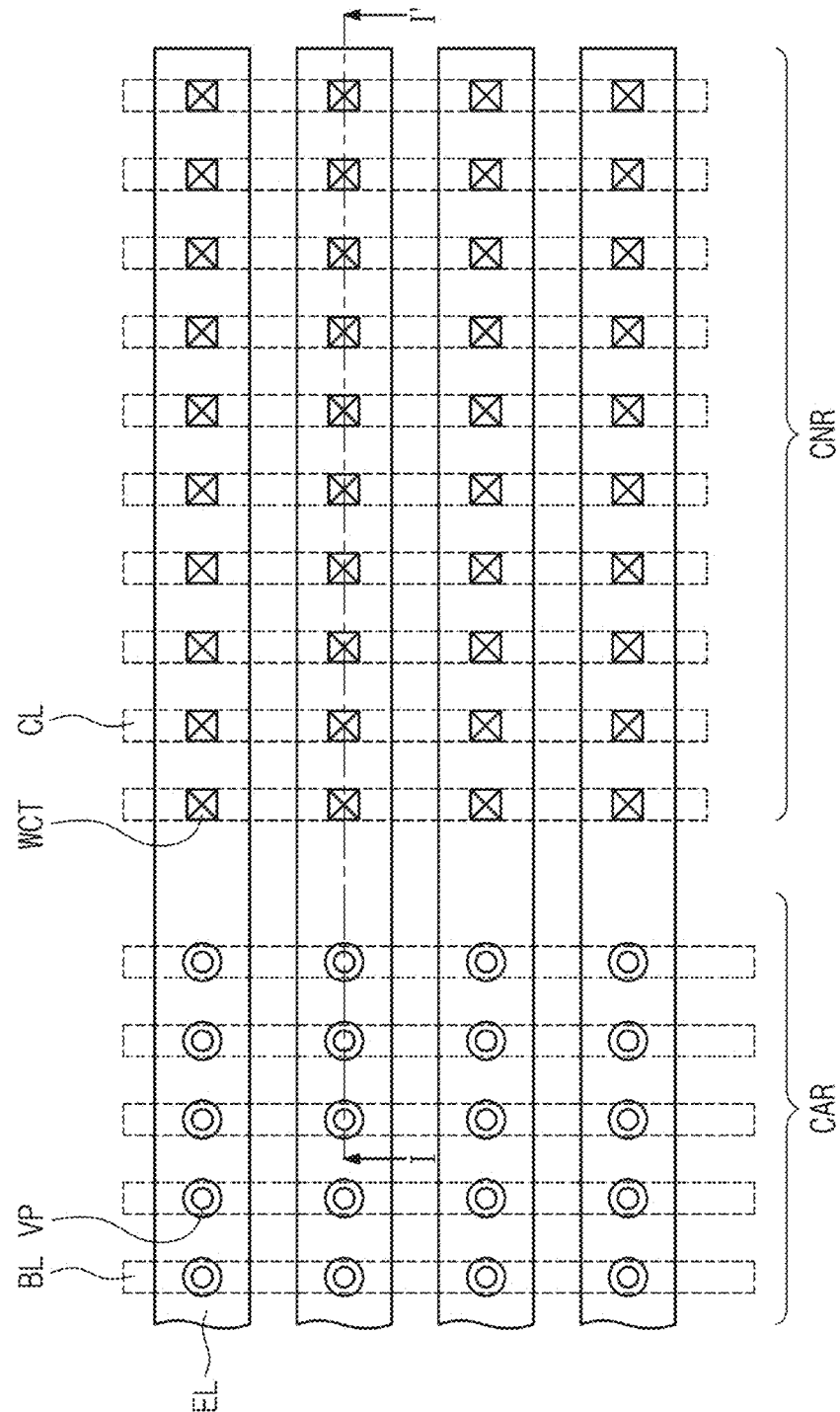
FIG. 14 is a plan view of a semiconductor device.

Hereinafter, a method of fabricating a semiconductor device using the above-described substrate inspection method will be described. FIG. 13 is a flow chart illustrating an example of a method of fabricating a semiconductor device according to the inventive concept. FIG. 14 is a plan view of an example of a semiconductor device, fabricated according to the inventive concept. FIGS. 15 to 21 are sectional views of the device during the course of its manufacture as taken in the direction of line I-I' of FIG. 14.

Figure 15:
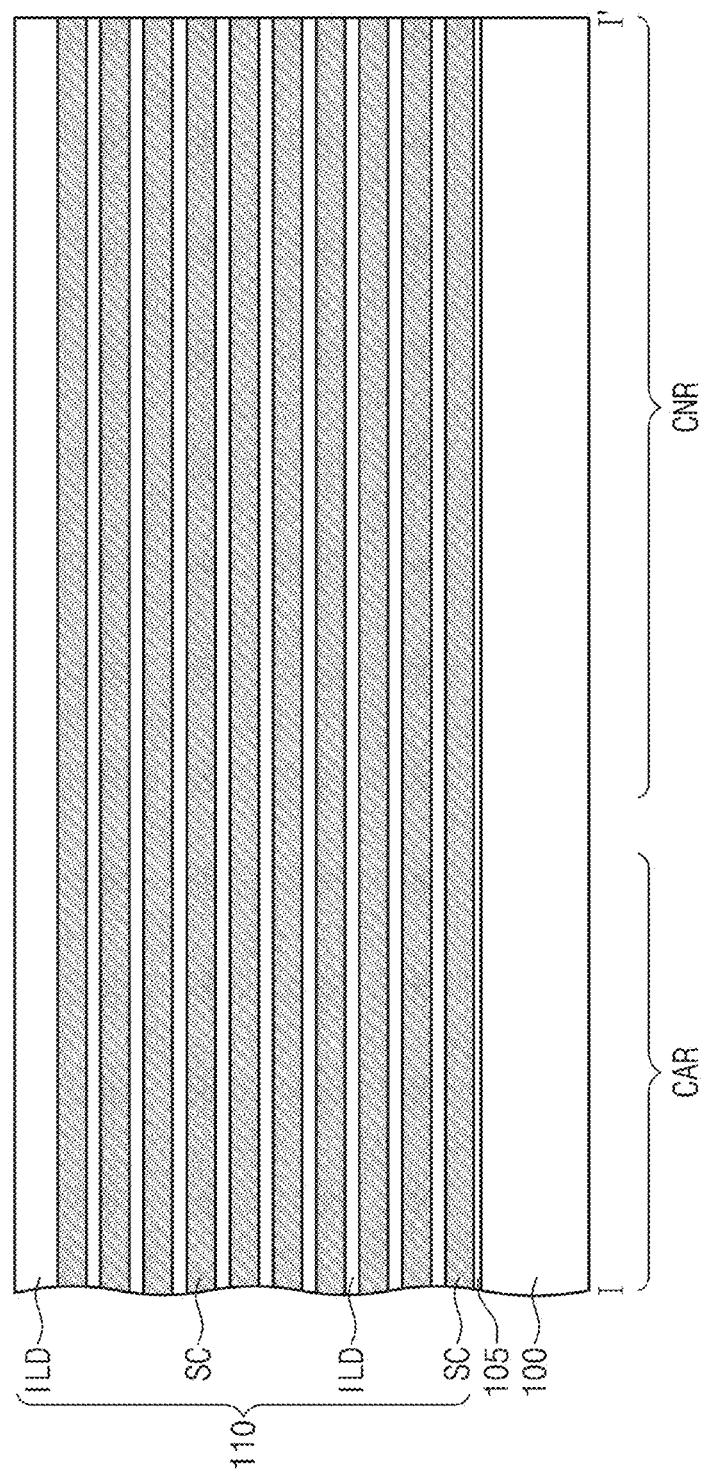
FIGS. 15, 16, 17, 18, 19, 20 and 21 are sectional views of the semiconductor device during the course of its manufacture, as taken in a direction corresponding to that of line I-I' of FIG. 14.

Referring to FIGS. 13, 14, and 15, a substrate 100 having a cell array region CAR and a connection region CNR may be provided. The substrate 100 may be a semiconductor substrate of a first conductivity type (e.g., p type).

A preliminary layered structure 110 may be formed on the substrate 100 (S110). The preliminary layered structure 110 may include sacrificial layers SC and insulating layers ILD, which are alternately and repeatedly stacked on the substrate 100. The sacrificial layers SC may be formed of or include a material that can be etched with an etch selectivity with respect to the insulating layers ILD. Each of the sacrificial layers SC may be formed of or include at least one of, for example, a silicon layer, a silicon carbide layer, a silicon oxynitride layer, or a silicon nitride layer. Each of the insulating layers ILD may be formed of or include at least one of a silicon layer, a silicon oxide layer, a silicon carbide layer, a silicon oxynitride layer, or a silicon nitride layer but may be formed of a material different from of the sacrificial layers SC. In some examples, the sacrificial layers SC are formed of silicon nitride layers, and the insulating layers ILD are formed of silicon oxide layers. In certain examples, the sacrificial layers SC are formed of silicon layers, and the insulating layers ILD are formed of silicon oxide layers. The sacrificial layers SC and the insulating layers ILD may be formed by, for example, a chemical vapor deposition method. The insulating layers ILD may have substantially the same thickness or at least one of the insulating layers ILD may have a different thickness from the others. For example, the uppermost layer of the insulating layers ILD may be thicker than the others of the insulating layers ILD.

A buffer insulating layer 105 may be formed on the substrate 100 before the preliminary layered structure 110. For example, the buffer insulating layer 105 may be a silicon oxide layer formed by a thermal oxidation process. In certain examples, the buffer insulating layer 105 is or includes a silicon oxide layer, which may be formed by a deposition process. The buffer insulating layer 105 may be formed to be thinner than each of the sacrificial layers SC and the insulating layers ILD thereon.

Figure 16:
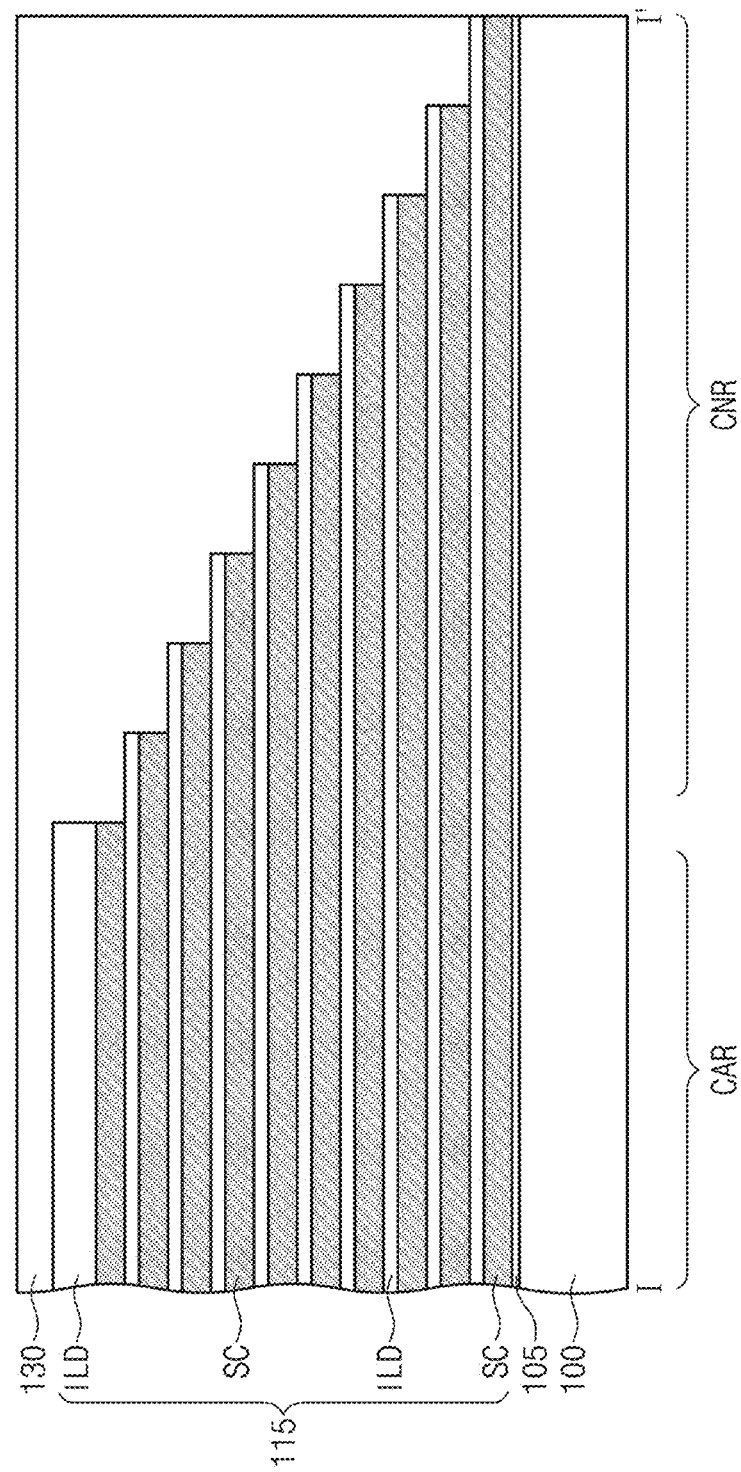

Referring to FIGS. 13, 14, and 16, the preliminary layered structure 110 may be patterned to form a layered structure 115 having a staircase portion (in S120). For example, the layered structure 115 may include end portions which are patterned to form a staircase structure on the connection region CNR. In some examples, the patterning of the preliminary layered structure 110 includes alternately and repeatedly performing steps of reducing a horizontal area of a mask pattern (not shown) and of anisotropically etching the preliminary layered structure 110. As a result of the steps performed alternately and repeatedly, end portions of the insulating layers ILD may be sequentially exposed on the connection region CNR. In other words, each of the insulating layers ILD may be formed to have an exposed top surface on the connection region CNR.

An insulating gapfill layer 130 may be formed on the substrate 100 to cover the layered structure 115. The insulating gapfill layer 130 may be formed by forming an insulating layer using a deposition method to cover the layered structure 115 and then performing a planarization process on the insulating layer. Accordingly, the insulating gapfill layer 130 may have a flat top surface. The insulating gapfill layer 130 may be formed of or include at least one of silicon oxide, silicon nitride, silicon oxynitride, or low-k insulating materials having dielectric constants lower than that of silicon oxide.

Figure 17:
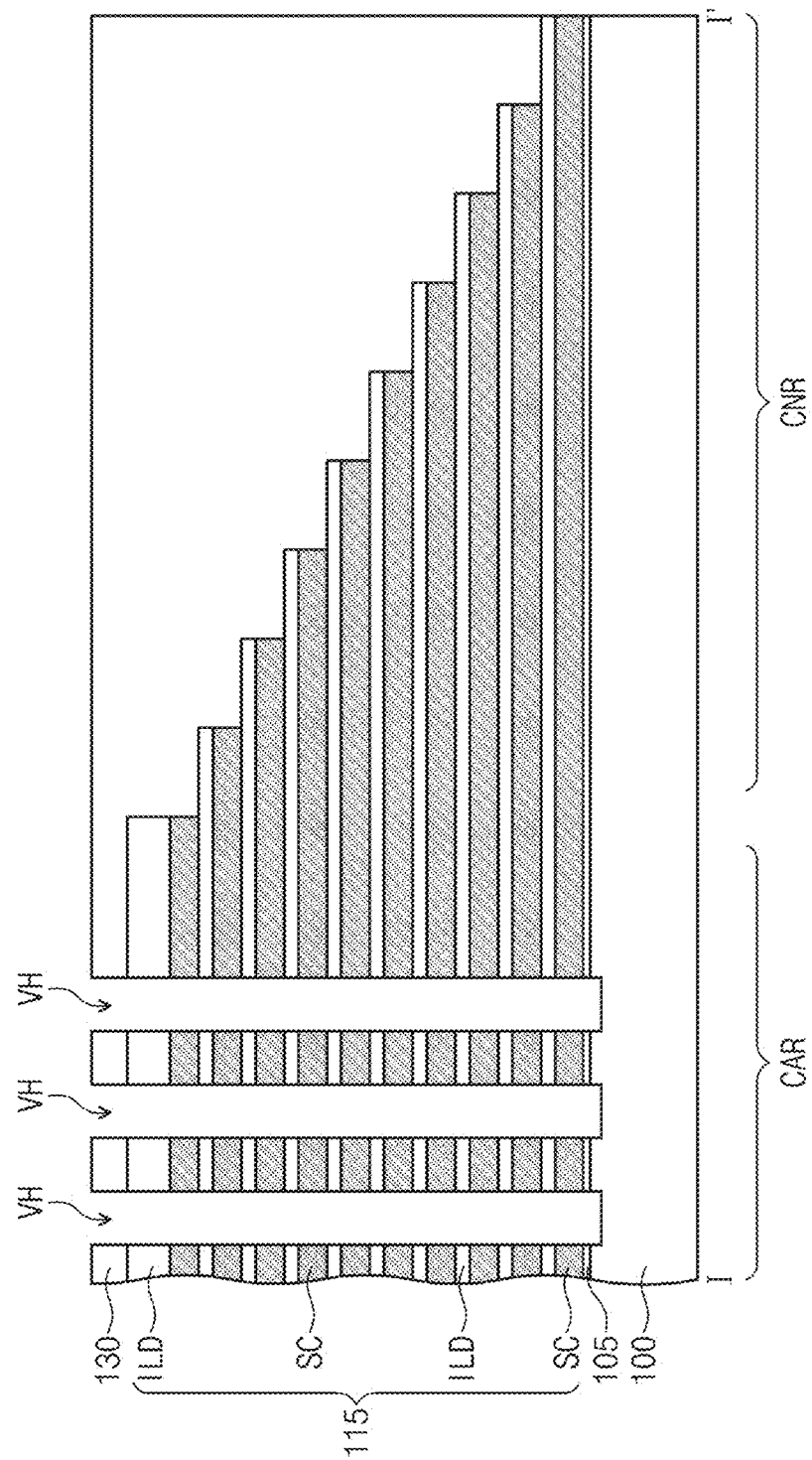

Referring to FIGS. 13, 14, and 17, vertical holes VH may be formed in the layered structure 115 to expose the cell array region CAR of the substrate 100 (in S130). In some examples, the vertical holes VH are formed by forming a mask pattern (not shown) on the layered structure 115 and performing an anisotropic etching process using the mask pattern as an etch mask. The anisotropic etching process may be performed to etch the top surface of the substrate 100 in an over-etch manner, and thus, portions of the substrate 100 may be recessed to a specific depth. The vertical holes VH may be formed to have a high aspect ratio. For example, the vertical holes VH may have an aspect ratio ranging from 1:5 to 1:100. Due to the high aspect ratio of the vertical holes VH, it may not be easy to realize high process uniformity in the etching process for forming the vertical holes VH. In some cases, therefore, the etching process may lead to a pattern failure of the vertical holes VH.

After the process of forming the vertical holes VH has been performed, a substrate inspection process may be performed (in S140). The substrate inspection process may be performed to examine whether there is a pattern failure of the vertical holes VH. For example, the substrate inspection process may be performed to examine non-uniformity in the aspect ratios of the vertical holes VH, variations in the diameters of the vertical holes VH at different vertical positions, bridge failures of (i.e., a bridge between) the vertical holes VH, or a not-open failure of the vertical hole VH. The substrate inspection process may be performed using the substrate inspection method described with reference to FIGS. 1 to 11. In this case, the operation for finding an optimized focus offset (value) may be executed using images of top surfaces of end portions of the layered structure 115 constituting the staircase portion. If, as described above, the substrate inspection method according to the inventive concept is used, it may be possible to more easily find an optimized focus offset and consequently to minimize the time required for the substrate inspection process. As a result, it may be possible to efficiently monitor a pattern failure according to a height or depth of the vertical hole VH, and a high quality semiconductor device may be fabricated with high productivity.

Figure 18:
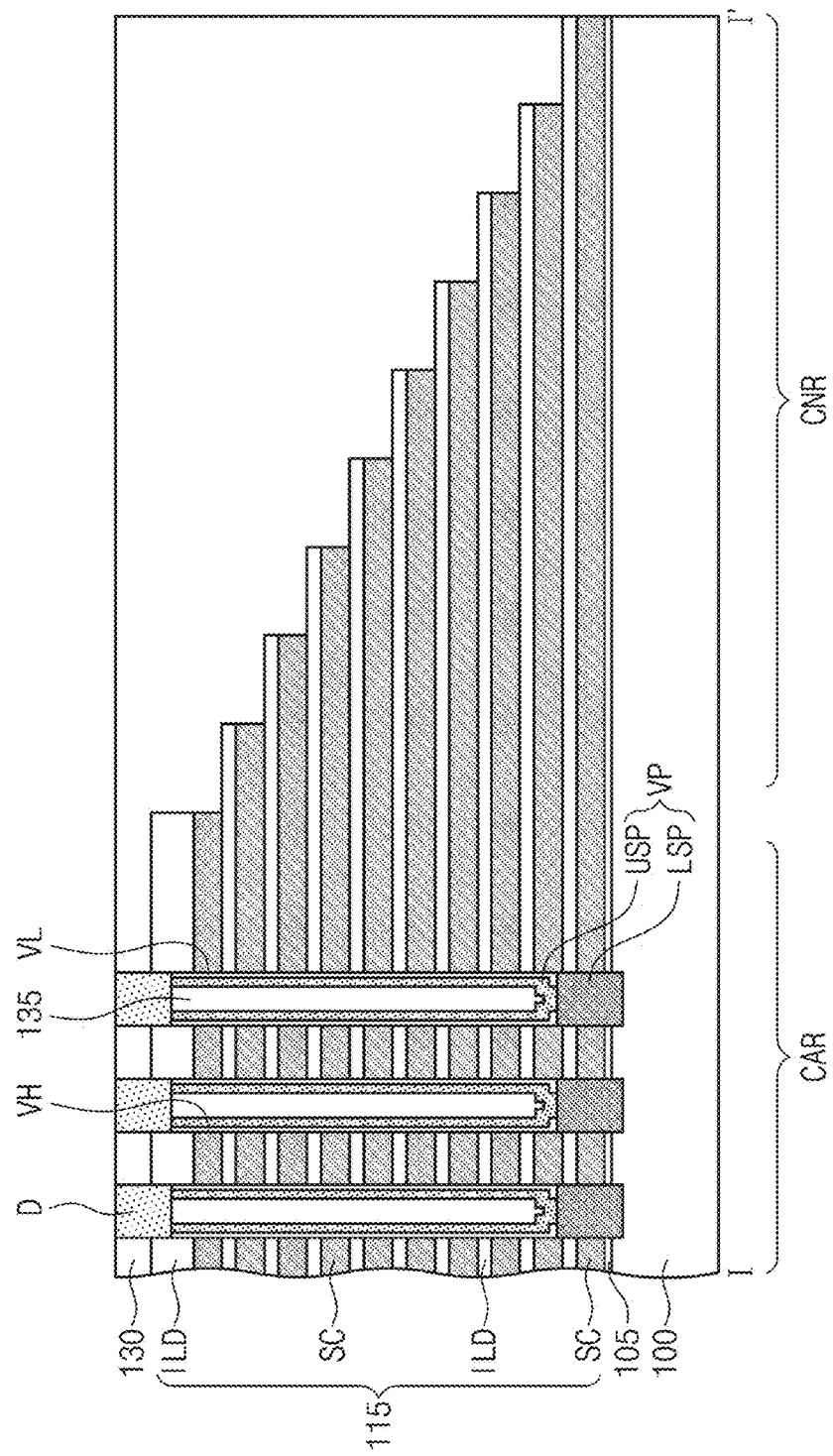

Referring to FIGS. 13, 14, and 18, vertical insulating layers VL and vertical pillars VP may be formed in the vertical holes VH (in S150). Each of the vertical insulating layers VL may include a plurality of insulating layers, and each of the vertical pillars VP may include a lower semiconductor pattern LSP and an upper semiconductor pattern USP.

For example, the lower semiconductor patterns LSP may be formed by a selective epitaxial growth (SEG) process, in which the substrate 100 exposed by the vertical holes VH is used as a seed layer. The lower semiconductor patterns LSP may be formed of a semiconductor material having the same conductivity type as that of the substrate 100 and may be pillar-shaped patterns filling lower regions of the vertical holes VH.

The vertical insulating layers VL and the upper semiconductor patterns USP may be sequentially formed on surfaces defining the sides of the vertical holes VH, in which the lower semiconductor patterns LSP are formed. Each of the vertical insulating layers VL may include a tunnel insulating layer, a charge storing layer, and a blocking insulating layer, which are sequentially stacked on the side of the vertical hole VH. The charge storing layer may be a charge trap layer or an insulating layer with conductive nano particles. More specifically, the charge storing layer may include at least one of, for example, a silicon nitride layer, a silicon oxynitride layer, a silicon-rich nitride layer, or a nano-crystalline silicon layer. The tunnel insulating layer may be formed of at least one insulating layer having a band gap greater than that of the charge storing layer. As an example, the tunnel insulating layer may be a silicon oxide layer. The blocking insulating layer may include at least one of a first blocking insulating layer, which is formed of or includes silicon oxide, and a second blocking insulating layer, which is formed of or includes a high-k dielectric material (e.g., aluminum oxide or hafnium oxide). The upper semiconductor pattern USP may be formed to have a hollow pipe or tubular shape. The upper semiconductor pattern USP may have a closed bottom portion. An internal space of the upper semiconductor pattern USP may be filled with an insulating layer 135. The upper semiconductor pattern USP may have a bottom surface that is positioned at a lower level than a top surface of the lower semiconductor pattern LSP. In other words, the upper semiconductor pattern USP may have a portion that is inserted into the lower semiconductor pattern LSP.

Conductive pads D may be formed on or in top portions of the vertical pillars VP. The conductive pads D may be formed by vertically recessing the top portions of the vertical pillars VP and filling the recessed regions with a conductive material. The conductive pads D may be formed by doping the top portions of the vertical pillars VP with impurities, and in this case, the conductive pads D may be formed to have a conductivity type (e.g., n-type) different from the vertical pillars VP. Thus, the conductive pads D and the vertical pillars VP thereunder may constitute diodes.

Figure 19:
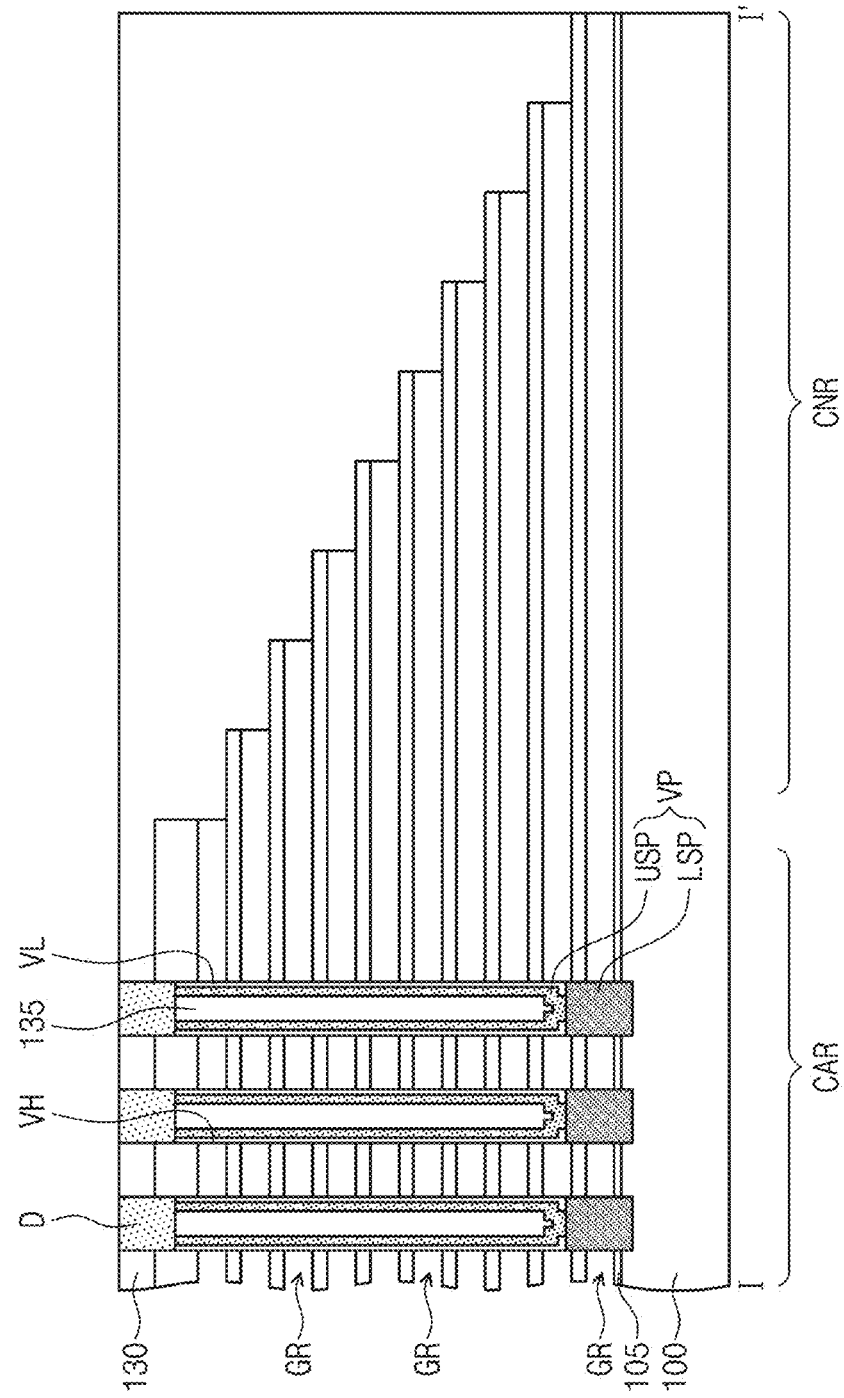

Referring to FIGS. 13, 14, and 19, the sacrificial layers SC may be removed to form gate regions GR between the insulating layers ILD (in S160). The gate regions GR may be formed by isotropically etching the sacrificial layers SC using an etch recipe having an etch selectivity with respect to the insulating layers ILD and vertical pillars VP. The sacrificial layers SC may be wholly removed by the isotropic etching process. For example, if the sacrificial layers SC are formed of silicon nitride and the insulating layers ILD are formed of silicon oxide, the isotropic etching process for removing the sacrificial layers SC may be performed using an etching solution including phosphoric acid. Although not shown, before the gate regions GR are formed, an isolation trench (not shown) may be formed through the layered structure 115 to expose the substrate 100, and the gate regions GR may be formed by selectively removing the sacrificial layers SC exposed by the isolation trench.

Figure 20:
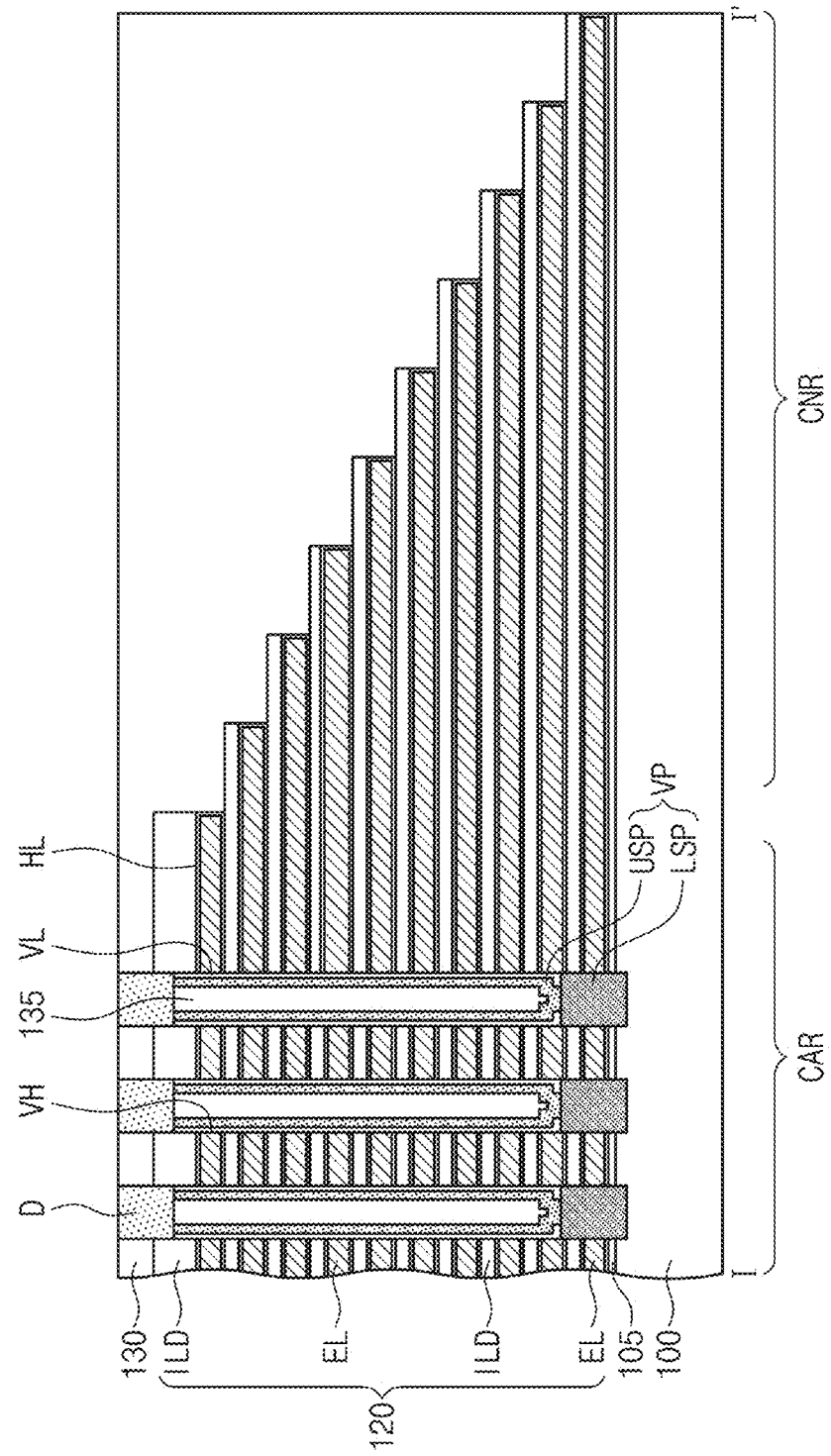

Referring to FIGS. 13, 14, and 20, gate electrodes EL may be formed in the gate regions GR (in S170). For example, the gate electrodes EL may be formed by forming a conductive layer in the gate regions GR through the isolation trench and removing the conductive layer from the isolation trench. The conductive layer may be formed of or include at least one of doped polysilicon, metal (e.g., tungsten), or conductive metal nitride (e.g., titanium nitride, tantalum nitride, or tungsten nitride). The conductive layer may be formed by an atomic layer deposition method. In some examples, before the conductive layer is formed, a horizontal insulating layer HL may be formed to conformally cover inner surfaces of the gate regions GR. For example, the horizontal insulating layer HL may be formed of a high-k dielectric layer (e.g., aluminum oxide and/or hafnium oxide).

Since the gate electrodes EL are formed in the gate regions GR, the gate electrodes EL and the insulating layers ILD may be alternately and repeatedly stacked on the substrate 100, thereby forming a stack 120.

Figure 21:
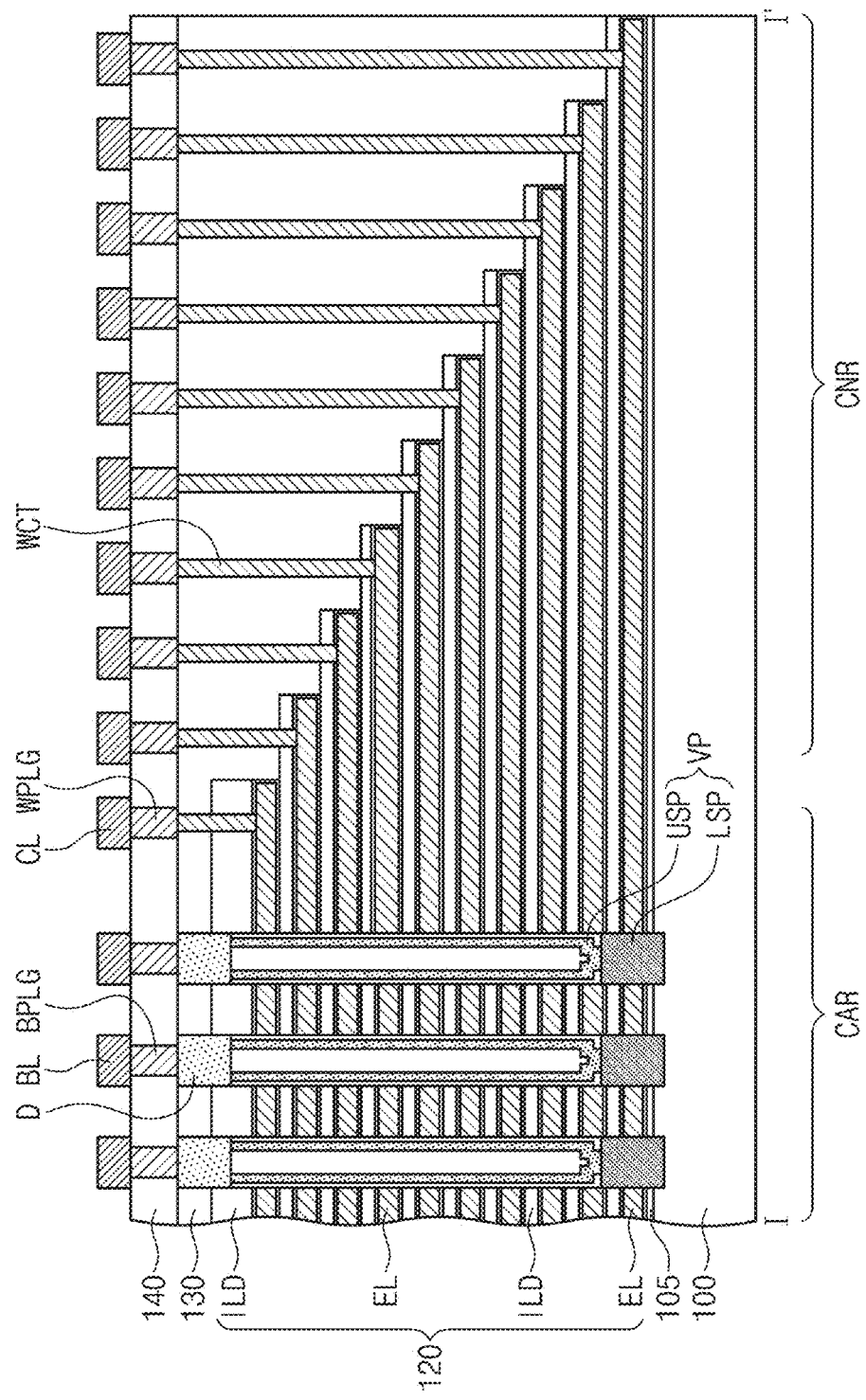

Referring to FIGS. 14 and 21, word line contacts WCT may be formed on the connection region CNR. The word line contacts WCT may be formed to extend through the insulating gapfill layer 130 and may be connected to end portions of the gate electrodes EL. The word line contacts WCT may be respectively connected to the gate electrodes EL positioned at different levels or heights. In other words, because the stack 120 has the staircase portion on the connection region CNR, the word line contacts WCT can be respectively connected to the end portions of the gate electrodes EL positioned at different levels.

An interlayered insulating layer 140 may be formed on the insulating gapfill layer 130, and bit line plugs BPLG may be formed to be connected to the vertical pillars VP of the cell array region CAR. In addition, word line plugs WPLG may be formed on the connection region CNR to be connected to the word line contacts WCT. Next, bit lines BL and connection lines CL may be formed on the interlayered insulating layer 140. The bit lines BL may be coupled to the bit line plugs BPLG, and the connection lines CL may be coupled to the word line plugs WPLG. For example, the bit lines BL and the connection lines CL may be formed by depositing a conductive layer on interlayered insulating layer 140 and patterning the conductive layer.

According to some examples of the inventive concept, when a three-dimensional structure (e.g., a stepwise or staircase structure) is formed on a substrate, the substrate inspection system may easily calculate a focus offset value, optimized for a vertical height of a defect desired to be detected, from images of top surfaces of the staircase structure. This may make it possible to minimize the time it takes to perform a process of inspecting a substrate and to effectively determine whether there is a failure in high-aspect-ratio patterns. Thus, the inventive concept may provide an improved inspection system and method.

In the case in which a semiconductor device is fabricated by a substrate inspection method according to the inventive concept, an optimized focus offset can be easily selected, and this may make it possible to minimize the time it takes for a substrate inspection process to be performed and to effectively monitor a semiconductor device for the occurrence of pattern failures during the manufacturing process. As a result, high quality semiconductor device can be fabricated with high productivity.

Although examples of the inventive concepts have been particularly shown and described, it will be understood by one of ordinary skill in the art that variations in form and detail may be made thereto without departing from the spirit and scope of the inventive concept as defined by the attached claims.

What is claimed is:

1. An inspection method for use in quality control of semiconductor devices, comprising:
   determining an optimal focus offset value;
   irradiating a layered structure on a substrate with incident light focused based on the optimal focus offset value, the layered structure comprising a first pattern having a top surface and an opening therein and a second pattern having top surfaces located at different heights relative to a top surface of the substrate, the opening extending in a direction perpendicular to a top surface of the substrate from the top surface of the first pattern;
   capturing an image of the layered structure from light reflected from the layered structure as a result of the irradiating of the layered structure; and
   detecting for a defect in the layered structure using the captured image of the layered structure,
   wherein the determining of the optimal focus offset value comprises:
   capturing focus offset images each of a region of the layered structure including the top surfaces of the second pattern while changing a focal position of the incident light, whereby the focus offset images are captured at different focal positions of the incident light; and
   calculating the optimal focus offset value using the focus offset images.

2. The method of claim 1, wherein the determining of the optimal focus offset value comprises:
   selecting regions of the focus offset images as comparison regions, respectively;
   quantifying the contrast of each of the comparison regions of the focus offset images;
   determining which of the comparison regions has the greatest contrast; and
   basing the optimal focus offset value on a focus offset value of the focus offset image whose comparison region has the greatest contrast among the comparison regions of the focus offset images.

3. The method of claim 2, wherein the focus offset value corresponds to a distance, along an optical axis along which the incident light propagates, between a predetermined reference focal position and the focal position of the focus offset image whose comparison region has the greatest contrast among the comparison regions of the focus offset images.

4. The method of claim 2, wherein the comparison regions of the focus offset images are each of a region of a same one of the top surfaces of the second pattern, closest to a vertical position of a defect desired to be detected.

5. The method of claim 4, wherein the defect desired to be detected is a pattern failure of the opening.

6. The method of claim 5, wherein the pattern failure of the opening is a not-open failure of the opening, and
   the comparison regions of the focus offset images are each a region of the lowermost one of the top surfaces of the second pattern.

7. The method of claim 1, wherein the determining of the optimal focus offset value further comprises performing a substrate alignment operation of adjusting a position of the substrate in a plane perpendicular to an optical axis along which the incident light propagates, before the capturing of the focus offset images.

8. The method of claim 1, wherein the top surfaces of the second pattern constitute a staircase portion having a height that decreases with an increase in distance in a given a direction from the first pattern.

9. The method of claim 1, wherein the detecting for the defect in the layered structure on the substrate comprises:
determining a detection focal position using the optimal focus offset value; and
scanning the substrate with light focused at the detection focal position.

10. The method of claim 9, wherein the detection focal position is obtained by adding or subtracting the optimal focus offset value to or from a predetermined reference focal position.

11. A method of fabricating a semiconductor device, comprising:
forming a preliminary structure comprising a stack of layers on a substrate;
patterning the preliminary structure to form a layered structure having a staircase portion constituted by ends of the layers, and a pattern of vertical holes in the layers to expose the substrate; and
performing a substrate inspection process,
wherein the substrate inspection process comprises:
determining an optimal focus offset value;
irradiating the layered structure with incident light focused based on the optimal focus offset value;
capturing an image of the pattern of vertical holes from light reflected from the layered structure as a result of the irradiating of the layered structure; and
detecting for a defect in the vertical holes using the captured image of the pattern of vertical holes;
wherein the determining of the optimal focus offset value comprises:
capturing focus offset images each of a region of the layered structure including top surfaces of the ends of the layers while changing the focal position of the incident light, whereby the focus offset images are captured at different focal positions of the incident light; and
calculating the optimal focus offset value using the focus offset images.

12. The method of claim 11, wherein the determining of the optimal focus offset value comprises:
selecting regions of the focus offset images as comparison regions, respectively;
quantifying the contrast of each of the comparison regions of the focus offset images;
determining which of the comparison regions has the greatest contrast; and
basing the optimal focus offset value on a focus offset value of the focus offset image whose comparison region has the greatest contrast among the comparison regions of the focus offset images.

13. The method of claim 12, wherein the comparison regions of the focus offset images are each of a region of a same one of the top surfaces of the ends of the layers, closest to a vertical position of a defect desired to be detected.

14. The method of claim 11, wherein the layers include insulating layers and sacrificial layers alternately and repeatedly stacked on the substrate.

15. The method of claim 14, further comprising:
forming vertical insulating layers and vertical pillars in the vertical holes;
selectively removing the sacrificial layers to form gate regions; and
forming gate electrodes in the gate regions, respectively.

16. An inspection method for use in quality control of semiconductor devices, comprising:
providing a target for inspection, the target including a substrate and a layered structure on the substrate, the layered structure having a pattern of openings exposed at a top surface of the layered structure and a stepped portion having exposed top surfaces disposed at different levels relative to the substrate
determining an optimal focus offset value;
imaging the layered structure based on the optimal focus offset value to obtain a representation of the pattern of openings; and
analyzing the representation of the pattern of holes to determine whether a defect is present in a region of the layered structure including the pattern of holes,
wherein the determining of the optimal focus offset value comprises:
irradiating a region of the layered structure including the top surfaces of the stepped portion with incident light focused at a focal position spaced a distance from a top surface of the substrate,
incrementally changing the focal position to vary the distance at which the focal position is spaced from the top surface of the substrate,
capturing an image of said region of the layered structure at each time the focal position has been incrementally changed, whereby a plurality of focus offset images are acquired, each of the focus offset images being an image of said region of the layered structure captured from light reflecting from the layered structure as a result of the layered structure having been irradiated with the incident light focused at a respective focal position, and
calculating the optimal focus offset value using the focus offset images.

17. The method of claim 16, wherein the determining of the optimal focus offset value comprises:
selecting vertically corresponding portions of the focus offset images as comparison regions, respectively;
determining which of the comparison regions has the greatest contrast; and
basing the optimal focus offset value on the focal position at which the focus offset image, whose comparison region has the greatest contrast among the comparison regions of the focus offset images, was captured.

18. The method of claim 16, wherein the incremental changing of the focal position comprises loading the target for inspection on a stage, and moving the stage and an objective lens, through which the incident light is transmitted, relative to one another.

19. The method of claim 16, wherein the imaging of the layered structure based on the optimal focus offset value comprises deriving a plurality of detection focal positions from the optimal focus offset value, sequentially focusing the incident light on the layered structure at the detection focal positions, and capturing an image of the layered structure each time the layered structure is irradiated with the incident light focused at one of the detection focal positions.

20. A method of manufacturing a semiconductor device, comprising:
performing the inspection method as claimed in claim 16; and subsequently forming a vertical insulating layer and a vertical layer of semiconductor material in each of respective ones of the openings.

\* \* \* \* \*